(12) United States Patent
Shalev

(10) Patent No.: US 12,313,585 B2
(45) Date of Patent: May 27, 2025

(54) ELECTRONIC SENSOR FOR USE IN SOLUTION CONTENT ANALYSIS AND METHOD FOR OPERATING THE SAME

(71) Applicant: B.G. NEGEV TECHNOLOGIES & APPLICATIONS LTD., AT BEN-GURION UNIVERSITY, Beer-Sheva (IL)

(72) Inventor: Gil Shalev, Ramat Hasharon (IL)

(73) Assignee: B.G. NEGEV TECHNOLOGIES & APPLICATIONS LTD., AT BEN-GURION UNIVERSITY, Beer-Sheva (IL)

( * ) Notice: Subject to any disclaimer, the term of this patent is extended or adjusted under 35 U.S.C. 154(b) by 552 days.

(21) Appl. No.: 17/634,776

(22) PCT Filed: Aug. 12, 2020

(86) PCT No.: PCT/IL2020/050880
§ 371 (c)(1),
(2) Date: Feb. 11, 2022

(87) PCT Pub. No.: WO2021/028913
PCT Pub. Date: Feb. 18, 2021

(65) Prior Publication Data
US 2022/0276195 A1    Sep. 1, 2022

Related U.S. Application Data

(60) Provisional application No. 62/894,803, filed on Sep. 1, 2019, provisional application No. 62/885,841, filed on Aug. 13, 2019.

(51) Int. Cl.
*G01N 27/327*  (2006.01)
*G01N 33/543*  (2006.01)

(52) U.S. Cl.
CPC ..... *G01N 27/3272* (2013.01); *G01N 27/3273* (2013.01); *G01N 33/5438* (2013.01)

(58) Field of Classification Search
CPC .......... G01N 27/3272; G01N 27/3273; G01N 27/3276; G01N 27/4145; G01N 33/5438
See application file for complete search history.

(56) References Cited

U.S. PATENT DOCUMENTS

2004/0007740 A1\* 1/2004 Abstreiter .......... G01N 27/4145
257/347
2016/0131613 A1\* 5/2016 Jayant .................. C12Q 1/6869
257/253

(Continued)

FOREIGN PATENT DOCUMENTS

| WO | 2014/062799 | 4/2014 |
| WO | 2014/197891 | 12/2014 |
| WO | 2015/148981 | 10/2015 |

OTHER PUBLICATIONS

Khamaisi et al., Electrical performance of silicon-on-insulator field-effect transistors with multiple top-gate organic layers in electrolyte solution, ACS Nano, 2010, 4, 4601-460 (Year: 2010).\*

(Continued)

*Primary Examiner* — Luan V Van
*Assistant Examiner* — Shizhi Qian
(74) *Attorney, Agent, or Firm* — Nixon & Vanderhye PC

(57) ABSTRACT

In one aspect, the invention relates to an integrated circuit lab-on-chip bio-sensor, comprising: (a) a fluid compartment configured to receive a fluid; (b) a sensing layer at the bottom of the fluid compartment, the sensing layer has a top surface comprising molecules that are sensitive to target molecules of the fluid; (c) a readout structure in communication with the sensing layer, the readout circuit is configured to output a signal which is proportional to a sensing of target molecules by the sensing layer; and (d) at least one (Continued)

isolated electrode which is isolated from the fluid, the isolated electrode is configured to apply an electric field along at least an interface between the sensing layer and the fluid that in turn reduces or eliminates excess ion concentration along the interface during sensing.

24 Claims, 24 Drawing Sheets

(56) References Cited

U.S. PATENT DOCUMENTS

2016/0334362 A1* 11/2016 Liu .................. G01N 27/4148
2017/0184541 A1*  6/2017 Lin .................. G01N 33/54373
2017/0227533 A1*  8/2017 Lin .................. H01L 29/7831

OTHER PUBLICATIONS

Stoop R. L., Understanding silicon nanowire field-effect transistors for biochemical sensing, PhD thesis of Universität Basel, 2016 (Year: 2016).*

Tarasov et al., True reference nanosensor realized with silicon nanowires, Langmuir, 2012, 28, 9899-9905 (Year: 2012).*

Wang et al., Oxide-on-graphene field effect bio-ready sensors, Nano Research, 2014, 7, 1263-1270 (Year: 2014).*

Aug. 9, 2023 Search Report issued in European Patent Application No. 20852373.8, pp. 1-9.

Napoli et al., "Electronic Detection of DNA Hybridization by Coupling Organic Field-Effect Transistor-Based Sensors and Hairpin-Shaped Probes," vol. 18, No. 4, Mar. 27, 2018, pp. 1-8.

International Search Report for PCT/IL2020/050880 dated Nov. 30, 2020, 4 pages.

Written Opinion of the ISA for PCT/IL2020/050880 dated Nov. 30, 2020, 5 pages.

Chu et al., Beyond the Debye length in high ionic strength solution: direct protein detection with field-effect transistors (FETs) in human serum, Scientific Reports, vol. 7, 2017, Article No. 5256, Online ISSN 2045-2322, pp. 1-15, Jul. 12, 2017.

Bhattacharyya et al., Electrostatically Governed Debye Screening Length at the Solution-Solid Interface for Biosensing Applications, ACS Sensors, vol. 5, Issue 1, pp. 154-161, Web Edition ISSN 2379-3694, Dec. 27, 2019.

* cited by examiner

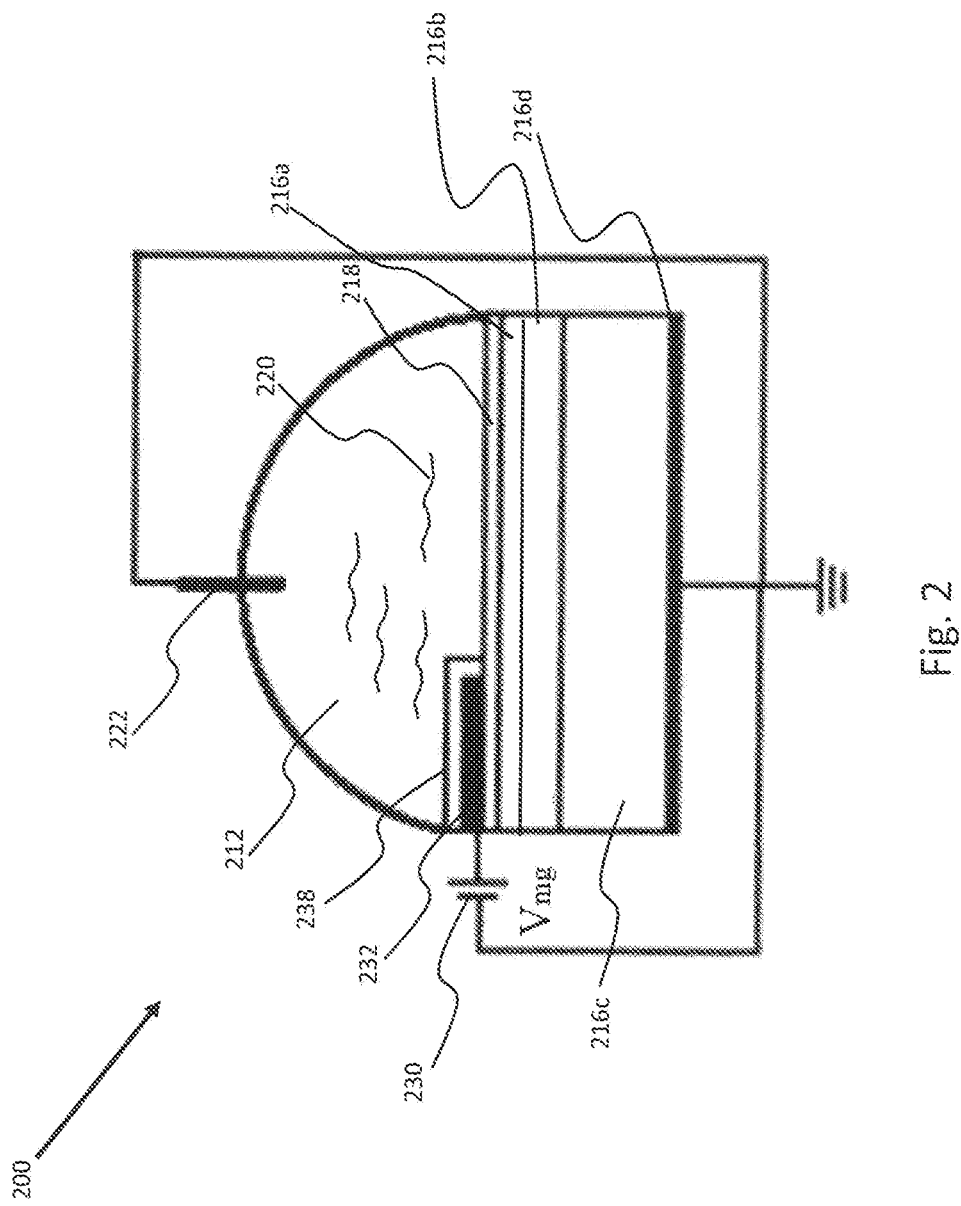

ELECTRONIC SENSOR FOR USE IN SOLUTION CONTENT ANALYSIS AND METHOD FOR OPERATING THE SAME

This application is the U.S. national phase of International Application No. PCT/IL2020/050880 filed Aug. 12, 2020 which designated the U.S. and claims priority to U.S. Provisional Application No. 62/894,803 filed Sep. 1, 2019, and U.S. Provisional Application No. 62/885,841 filed Aug. 13, 2019, the entire contents of each of which are hereby incorporated by reference.

FIELD OF THE INVENTION

The invention relates in general to lab-on-chip sensors for use in the analysis of solution ingredients. More specifically, the invention relates to a sensor in the form of an integrated circuit for sensing one or more ingredients of a solution.

BACKGROUND OF THE INVENTION

Lab-on-chip biosensors are integrated circuits that convert a biological status of a fluid (gas or liquid) to an electrical signal which is indicative of one or more of the fluid's ingredients. For example, a bio-sensor may check the presence of selected target molecules (e.g., DNA hybridization, antibody-protein interaction, etc.) in a solution. Typically, lab-on-chip biosensors include a fluid compartment for containing the analyzed fluid (either permanently or during flow), a sensing layer for producing an indicative signal, and a readout module that receives, amplifies, and outputs the indicative signal. In principle, the sensing layer is a coating on a front surface of the readout circuit (towards the solution). The sensing layer typically includes "capturing molecules" that are selected to "capture" specific molecules from the solution. The interaction with the solution modifies the electrostatics at the interface between the sensing layer and the solution, a change that forms a basis for the sensing signal at the output of the lab-on-chip sensor. The fluid compartment typically has an inlet and outlet, or another arrangement for refreshing the solution. Electronic biosensors that are based on field-effect components (bioFETs) offer numerous advantages over other technologies, therefore they have been a subject of immense research over the recent decades. BioFETs offer an attractive platform for the development of highly selective and sensitive lab-on-chip diagnostic sensors and point-of-care devices with a myriad of advantages such as dramatic miniaturization, superb detection limit, low power, ultra-small samples size, low cost, label-free, and real-time detection. These bioelectronic sensors are derivatives of the ion-sensitive FET (ISFET). The inherent electric charge or dipole of biomolecules inspires their direct detection using bioFETs. Generally, a bioFET is made sensitive to a specific target analyte, in one example, by immobilizing a bioreceptor layer on a gate oxide surface. Several works have demonstrated highly sensitive, specific, and label-free detection of biomolecules using bioFETs. However, despite significant efforts, their commercialization is very limited.

A very significant problem that is associated with this structure is the inherent concentration of ions in the interface between the solution and the sensing layer. The concentration of ions by itself corrupts the characteristics of the solution at the sensing interface, therefore producing non-physiological conditions at the interface with the sensing layer, in contrast to the real conditions at the rest of the fluid that the lab-on-chip intends to measure. This problem is reflected by three main issues: (a) A Debye screening region of non-sensing practically prohibits readout from the solution; (b) high electric fields at the sensing area in contrast with the trivial electric fields at the solution's bulk (the term "solution bulk" indicates a region remote from the Electrolyte-Oxide interface—EOI); and (c) the pH of the solution is corrupted at the interface, resulting in an inaccurate measurement.

The main challenge in the realization of bioFETs is the Debye screening in high ionic physiological solutions. When a charged biomolecule is positioned within the solution, it is surrounded, due to electrostatic interactions, by a cloud of solvent counter-ions that screens the charged biomolecules such that their intrinsic electrostatic potential decays exponentially with distance. This screening distance called the Debye length ($\lambda D$) is given by $$\lambda_D = \frac{1}{\sqrt{4\pi l_B N_{Av} \Sigma_i \rho_{B,i} z_i^2}}$$

where $l_B$ is the Bjerrum length=0.7 nm for room temperature. This is the length at which thermal energy is equal to the Coulombic energy between two unit charges, $N_{Av}$ is the Avogadro's number, $z_i$, and $\rho_B$, i are the valence and bulk concentration of ion species i, respectively, and the sum extends over all ion species in the solution. In typical physiological samples, $\lambda_D$ is approximately 0.7-2.2 nm which does not significantly hamper the detection of small molecules like DNA oligonucleotides. Yet, in a case of larger receptor molecules like antibodies (10-15 nm), the dimensions imply that the detection of antigens using bioFETs is severely incapacitated. Consequently, for FET-based macro biomolecules detection in whole blood samples or serum, either the ionic strength of the medium has to be greatly reduced, or smaller bio-receptors must be utilized. It has already been demonstrated that the ionic strength of the buffer solution should be carefully selected to optimize bioFET sensitivity. Recently, it was demonstrated that smaller nanowires with high Debye volume-to-surface ratio face higher ionic screening, as a higher concentration of ions can approach the sensing area due to increased surface convexity.

To circumvent the Debye screening in bioFETs, most prior art devices perform the biosensing in dilute solutions. However, the dilution of buffer solutions may potentially affect the biomolecule conformation and result in loss of target analyte activity and binding affinity. Furthermore, it requires complex, time-consuming manipulation steps such as ex-situ desalination processes. The prior art has proposed various bioreceptor engineering methods to utilize antibody fragments or aptamers. Other solutions that have been proposed are chemistry-related. However, while partially resolving one specific aspect of the problem, other issues have been remained unresolved, as none of the prior art methods has eliminated the concentration of ions at the interface between the solution and the sensing layer to a satisfactory level.

It is, therefore, an object of the present invention to eliminate the inherent concentration of ions at the interface between the solution and the biosensor, a concentration that causes a corruption of the sensing in terms of (a) a short Debye screening length; (b) high electric fields at the surface, and (c) corruption of the pH which is different at the proximity of the sensing layer compared to the pH at the entire solution.

It is another object of the invention to provide a variety of lab-on-chip structures that eliminate said inherent concentration at the interface between the solution and the sensing layer.

It is still another object of the invention to provide lab-on-chip structures that not only eliminate the inherent concentration of ions at the interface between the solution and the sensing layer, but also to provide structures for performing various additional manipulations on the solution that are not available in prior art devices.

Other objects and advantages of the invention will become apparent as the description proceeds.

SUMMARY OF THE INVENTION

In one aspect, the invention relates to an integrated circuit lab-on-chip bio-sensor, comprising: (a) a fluid compartment configured to receive a fluid; (b) a sensing layer at the bottom of the fluid compartment, the sensing layer has a top surface comprising molecules that are sensitive to target molecules of the fluid; (c) a readout structure in communication with the sensing layer, the readout circuit is configured to output a signal which is proportional to a sensing of target molecules by the sensing layer; and (d) at least one isolated electrode which is isolated from the fluid, the isolated electrode is configured to apply an electric field along at least an interface between the sensing layer and the fluid that in turn reduces or eliminates excess ion concentration along the interface during sensing.

In an embodiment of the invention, the isolated electrode is positioned on top of the sensing layer.

In an embodiment of the invention, the at least one isolated electrode is a metal electrode.

In an embodiment of the invention, the readout structure comprising a gate-oxide (gateox) layer on top of a Silicon on Insulator (SOI) structure.

In an embodiment of the invention, the SOI structure comprising an SOI layer, a buried-oxide (box) layer, a handle layer, and a back-gate layer.

In an embodiment of the invention, one or more of the isolated electrodes are embedded within the SOI layer or positioned on top of the gateox layer.

In an embodiment of the invention, the sensing layer includes receptor molecules that are designed to capture target molecules from the fluid.

In an embodiment of the invention, the bio-sensor further comprising one or more non-isolated electrodes on top of the sensing layer, the non-isolated electrodes are configured to have contact with the solution.

In an embodiment of the invention, the one or more non-isolated electrodes on top of the sensing layer are configured to receive voltage adapted to cause a surface current between two or more of the non-isolated electrodes, or a solution current between the one or more non-isolated electrodes and one or more reference or counter electrodes on a cover of the fluid compartment, thereby to affect the interaction of the receptors and/or target molecules within the sensing layer or solution, respectively.

In an embodiment of the invention, the readout circuit is selected from a FET-type, capacitance-voltage measurement, or electrochemical impedance spectroscopy.

In an embodiment of the invention, the fluid compartment comprising a fluid inlet and fluid outlet that are configured to support a fluid flow through the compartment.

In another aspect, the invention relates to a method for operating a bio-sensor, the biosensor comprising a fluid compartment, a sensing layer, and a readout circuit, the method comprising: (a) providing fluid at the fluid compartment; (b) providing one or more isolated electrodes that are isolated from the fluid; (c) effecting via the or more isolated electrodes an electric field in a region which includes at least an interface between the sensing layer and the fluid.

In an embodiment of the invention, the electric field eliminates the accumulation of ions in the interface between the sensing layer and the solution.

In an embodiment of the invention, the electric field and the elimination of the accumulation of ions at the interface between the sensing layer and the solution also affects one or more of: (a) the pH level at the interface to match to the pH at the bulk of the fluid; (b) reduction of the surface ion density to match the ion density at the bulk of the fluid; and (c) reduction of the electric field at the interface to match the electric field at the bulk of the fluid.

In an embodiment of the invention, the elimination of the accumulation of ions increases the Debye screening length.

In an embodiment of the invention, the elimination of the accumulation of ions produces a homogenous region within the entire solution in terms of charge carries.

In one embodiment, the method further comprising providing receptors at the sensing layer that are configured to selectively capture target molecules from within the fluid.

In one embodiment, the method further comprising the generation of one or more current flows through the fluid to manipulate orientations of the receptors and/or target molecules, thereby to increase the probability of target molecules capturing by the receptors.

In one embodiment, the current flows are generated in between two or more non-isolated electrodes, at least some of them being located on the sensing layer or on a cover of the fluid compartment.

In one embodiment, the current flows are selected from: (a) surface currents along the surface of the sensing layer between two or more of non-isolated electrodes on top of the sensing layer; and (b) fluid current flows between one or more of non-isolated electrodes on top of the sensing layer and one or more non-isolated electrodes on a cover of a fluid compartment of the biosensor.

In one embodiment, the one or more current flows through the fluid are provided in a first stage to manipulate interactions of the receptors and/or target molecules, and the electric field is provided in a second, readout stage to increase a Debye length at the interface.

In one embodiment the method comprising providing in a first stage a voltage to the one or more isolated electrodes to affect surface electric fields, surface pH level, or surface ion density, and in a second readout stage providing the electric field to increase a Debye length at the interface.

In one embodiment, a voltage that is provided to the one or more isolated electrodes is DC or AC voltage.

In one embodiment, the currents are either DC or AC currents.

BRIEF DESCRIPTION OF THE DRAWINGS

In the drawings:

FIG. 2 shows a biosensor system 200 according to an embodiment of the invention;

FIG. 4b shows a numerically calculated hole density distribution in the structure of FIG. 4a;

FIG. 4c shows a numerically calculated electric field distribution in the system of FIG. 4a;

FIGS. 5b-1 to 5b-3 illustrate three possible structures of a biosensor of the invention in a cross-section view made along line A-A of FIG. 5a;

DETAILED DESCRIPTION OF PREFERRED EMBODIMENTS

Figure 1:
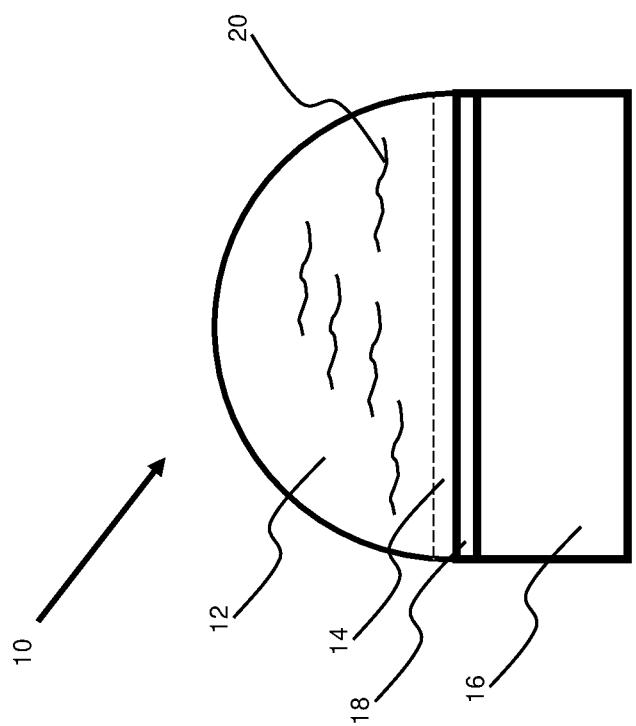
FIG. 1 shows a general structure of a prior art biosensor.

FIG. 1 shows a general structure of a prior art biosensor 10. The biosensor generally includes a fluid (liquid or gas) compartment 12, a sensing layer 18, and a readout module 16. The fluid compartment 12 typically includes inlet and outlet, for supporting a fluid 20 flow through the compartment. Alternatively, the fluid 20 may be contained stationary within the compartment, and replaced whenever necessary. The following description assumes that the fluid 20 is a biological solution, while parameters relating to one or more of the solution's ingredients have to be determined by the biosensor, however, other types of solutions, not necessarily for biological purposes, may be inspected by the device of the invention. The term "biosensor" which is used throughout this application should not be viewed as intending to limit the invention solely to biological purposes.

Sensing layer 18 typically includes "capturing molecules" that are selected to "capture" specific or non-specific molecules from the solution. The interaction with the solution modifies the electrostatics at the interface between the sensing layer and the solution, an electrostatic modification that forms a basis for the sensing signal at the output of the lab-on-chip sensor. More specifically, the electrostatic modification is converted to an electrical signal and possibly amplified by the readout module 16. The readout module may include one or more layers of silicon (or another semiconductor material) and one or more electrodes. In one example, the readout module is a FET-type structure (but other types may be used). In still another example, the readout module is a FET-type which is arranged in an SOI (Silicon on Insulator) structure. The sensing layer 18 may be made of, for example, a layer of receptor molecules for specific or non-specific interaction with the target molecule.

As previously noted, the effectiveness of the solution ingredients' measurement is very significantly harmed due to an inherent concentration of ions in the interface 14 between the solution 20 and the surface of sensing layer 18. This inherent concentration of ions phenomenon harms the measurement in three main aspects: (a) A Debye screening region of non-sensing which is formed adjacent the interface practically prevents readout from the solution; (b) The concentration of ions by itself adjacent the sensing layer corrupts the characteristics of the solution at the solution-sensing layer interface, resulting in non-physiological conditions, that not necessarily reflects the true conditions at the main mass of the solution; and (c) similarly, the pH of the solution is corrupted at the interface, resulting in a measurement that does not reflect the true pH level at the main mass of the solution; and (d) high electric fields at the interface with the sensing area, in contrast with a substantially zero electric fields at the solution's bulk.

The inventors have developed an electrostatic approach for eliminating the concentration of ions at the solution-sensing layer interface. More specifically, the inventors have found that excess of surface ions can be eliminated by an application of voltage to an electrode that causes an electric field that extends to the EOI and the double layer (DL).

The invention provides a method and a biosensor structure for eliminating the concentration of ions in the proximity of the sensing layer. FIG. 2 shows a biosensor system 200 according to an embodiment of the invention. Again, the biosensor 201 includes a solution compartment 212, a sensing layer 218, and a readout structure 216. The solution may be, for example, electrolyte 220. Again, sensing layer 218 typically includes "capturing molecules" that are so selected to "capture" specific molecules from the solution. The interaction with the solution modifies the electrostatics at the interface between the sensing layer and the solution, an electrostatic modification that forms a basis for the sensing signal at the output of the lab-on-chip sensor. The electrostatic modification is converted to an electrical signal and possibly amplified by the readout module 216. The readout module may include one or more layers of silicon (or another semiconductor material) and one or more electrodes. In one example, the readout module is a FET-type structure (but other types may be used). In still another example, the readout module is a FET-type which is arranged in an SOI (Silicon on Insulator) structure. The sensing layer 218 may be made of, for example, a layer of receptor molecules for specific or non-specific interaction with the target molecule.

The biosensor of FIG. 2 includes a readout module 216 which is arranged in an SOI structure. The readout module 216 includes a gate-oxide layer 216a, a p-SOI (p-type silicon) layer 216b, a buried-oxide ("box") layer 216c, and a back gate 216d. A reference electrode 222 is provided at the top of the solution compartment 212 and is configured to be in contact with the solution 220. During operation, the reference electrode 222, as well as back gate 216d, are grounded in this specific example, however, this is not a requirement for all cases. Biosensor 200 also includes an electrode 232, in this case on top of the sensing layer 218, (other options for the location of the one or more electrode 232 will be discussed below). While the electrode 232 is in contact with the sensing layer 218, it is still isolated from the solution 220 by isolating cover 238. The isolated electrode 232 is used to provide voltage $V_{mg}$ to the sensing layer 218 (or to other layers, as will be discussed hereinafter). It has been found that the provision of voltage (in this specific case DC voltage) to the sensing layer 218 eliminates the inherent concentration of ions at the interface between the solution 220 and the sensing layer 218. This elimination of ions resolves all the three problems mentioned above, namely: (a) It eliminates the Debye screening region of non-sensing, by very significantly increasing the $\lambda_D$ to the solution bulk value; (b) It eliminates the high electric fields at the sensing area which is in contrast with the trivial (substantially zero) electric fields at the solution's bulk; and, (c) It causes the pH of the solution at the interface to be the same as in the main mass of the solution, and results in ion strength at the interface that is identical with the strength in the bulk solution.

Figure 3A:
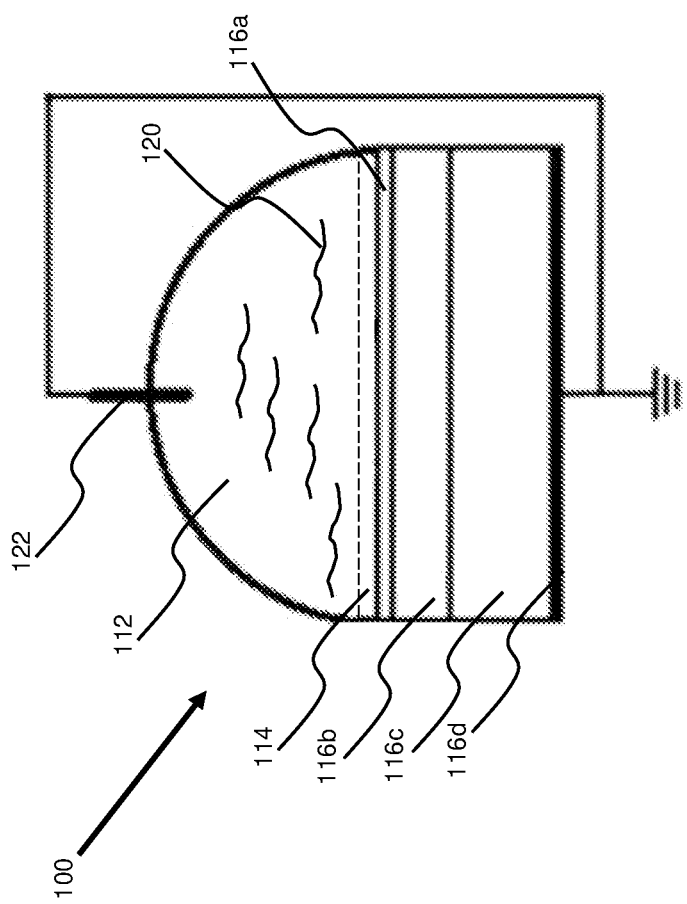
FIG. 3*a* shows numerical calculation results of a hole/counter ion density in a FET biosensor, without a provision of a voltage potential to the sensing layer.

Numerical calculations (hereinafter also referred to as "simulations") were performed to validate the efficiency and advantages of the invention. The following numerical calculations, as well as associated drawings, neither specifically discuss, nor specifically show the sensing layer. Instead, the effect of surface charge at the electrolyte-oxide-interface (EOI) was examined. The surface charge emulates the presence of charge introduced to the close vicinity of the EOI by the target molecule. Therefore, in the following numerical and analytical analysis, the presence of a sensing layer is disregarded. FIG. 3a shows a FET biosensor structure 100, without the provision of a voltage potential to the sensing layer (or to other layers that may affect the electric field in the proximity of the sensing layer). The biosensor includes a solution compartment 112, a sensing layer(not shown), and a readout module 116. The solution that was used during the numerical calculations was an electrolyte 120. In this specific simulation, an SOI structure was used for the readout module 116. The SOI module included a "gate oxide" (hereinafter also referred to as "gateox") 116a, a p-SOI (p-type silicon) layer 116b, buried-oxide ("box") layer 116c made of $SiO_2$, and a back-gate electrode 116d. A reference electrode 122 was provided at the top of the solution compartment 112 and was configured to contact the electrolyte solution 120. In the structure of FIG. 3a, the reference electrode 122, as well as the back gate 116d were grounded. The inherent concentration of ions (double layer) 114 at the region between the solution 120 and the gateox 116a was observed. Three separate interfaces were examined in the numerical calculations, as follows: (a) a solution-sensing layer interface (also referred to as "EOI" electrolyte-oxide interface); (b) a front-interface between the rear surface of the gateox 116a (i.e., the surface of the gateox away from the solution) and the p-SOI layer 116b; and (c) a back-interface between the rear of the p-SOI layer 116b and the buried-oxide layer 116c.

Figure 3B:
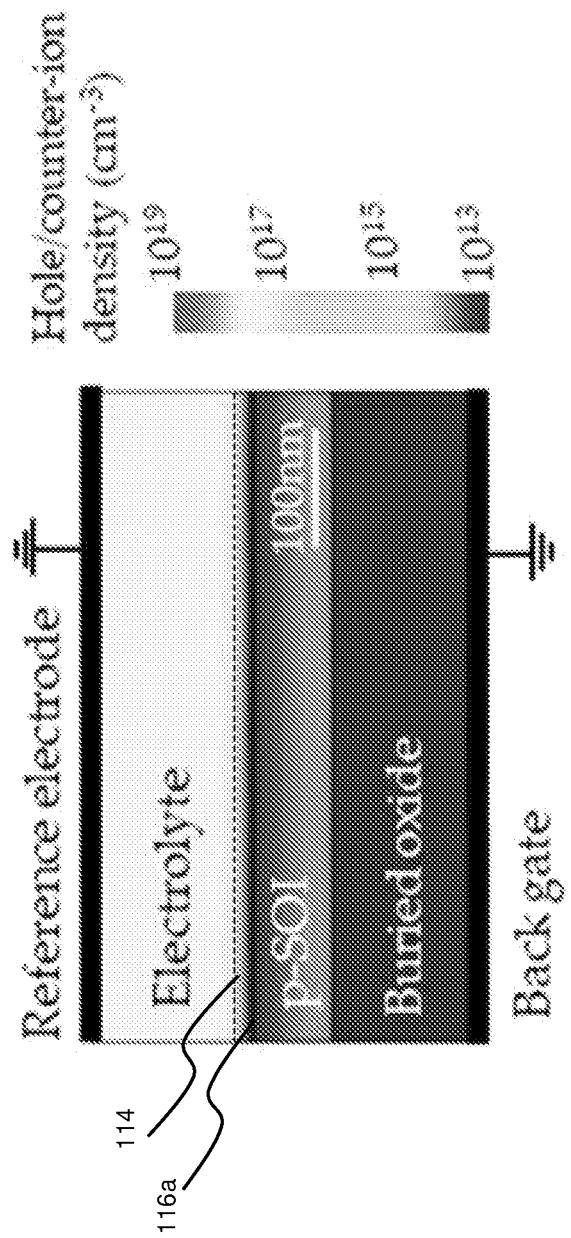
FIG. 3*b* shows numerical calculation results of a hole/counter ion density in a FET biosensor, without a provision of a voltage potential to the sensing layer.
Figure 3C:
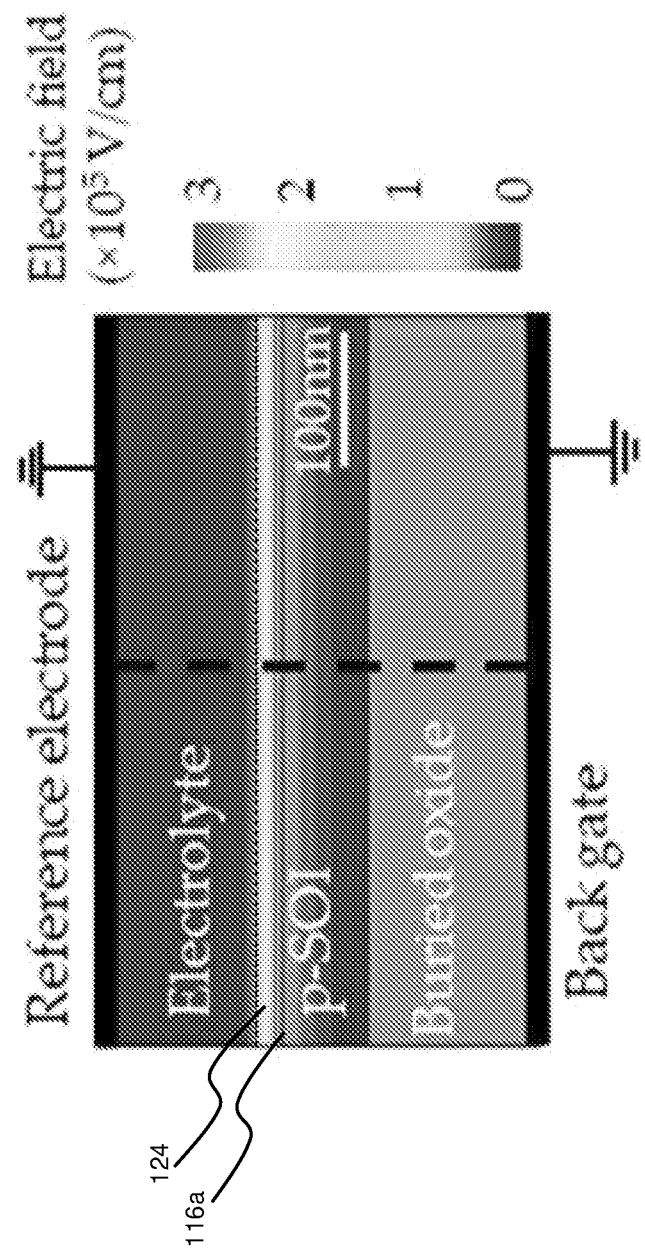
FIG. 3c shows numerical calculation results of an electric field in a FET biosensor, without a provision of a voltage potential to the sensing layer.
Figure 3D:
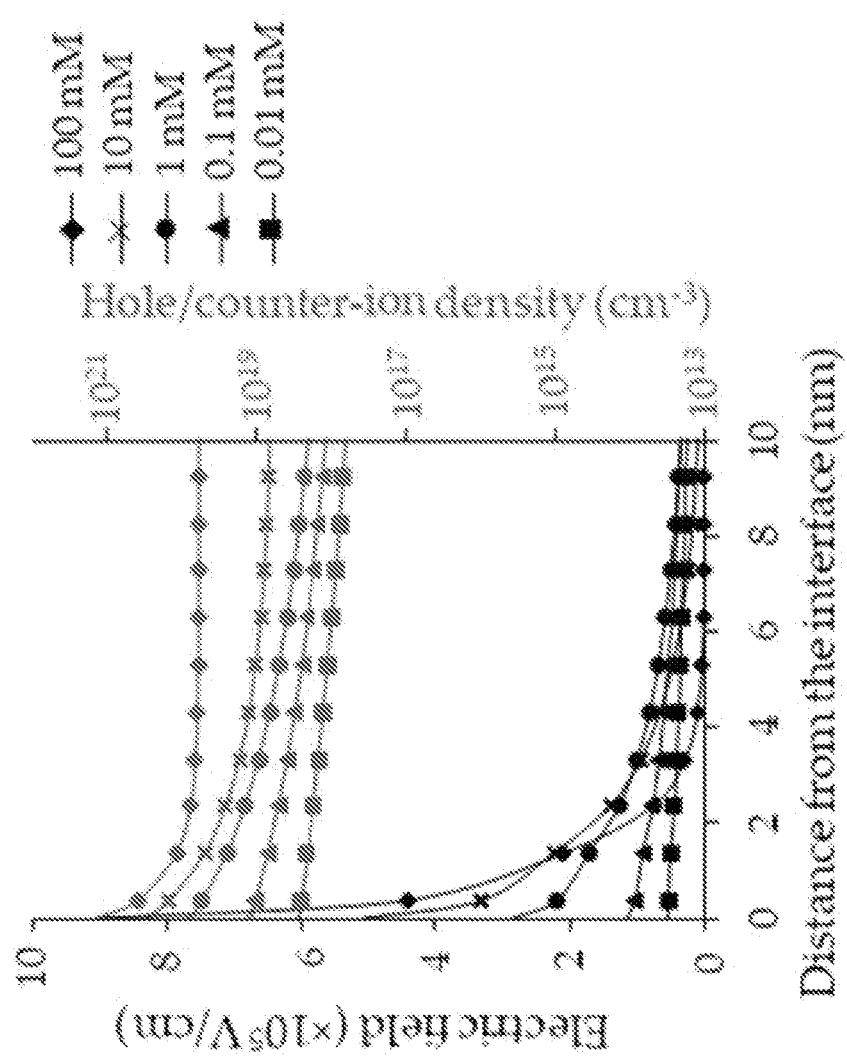
FIG. 3d shows numerically calculated variation of an electric field in an electrolyte solution for different ionic concentrations relative to the distance from the electrolyte-oxide interface (EOI) and towards the bulk solution.
Figure 3E:
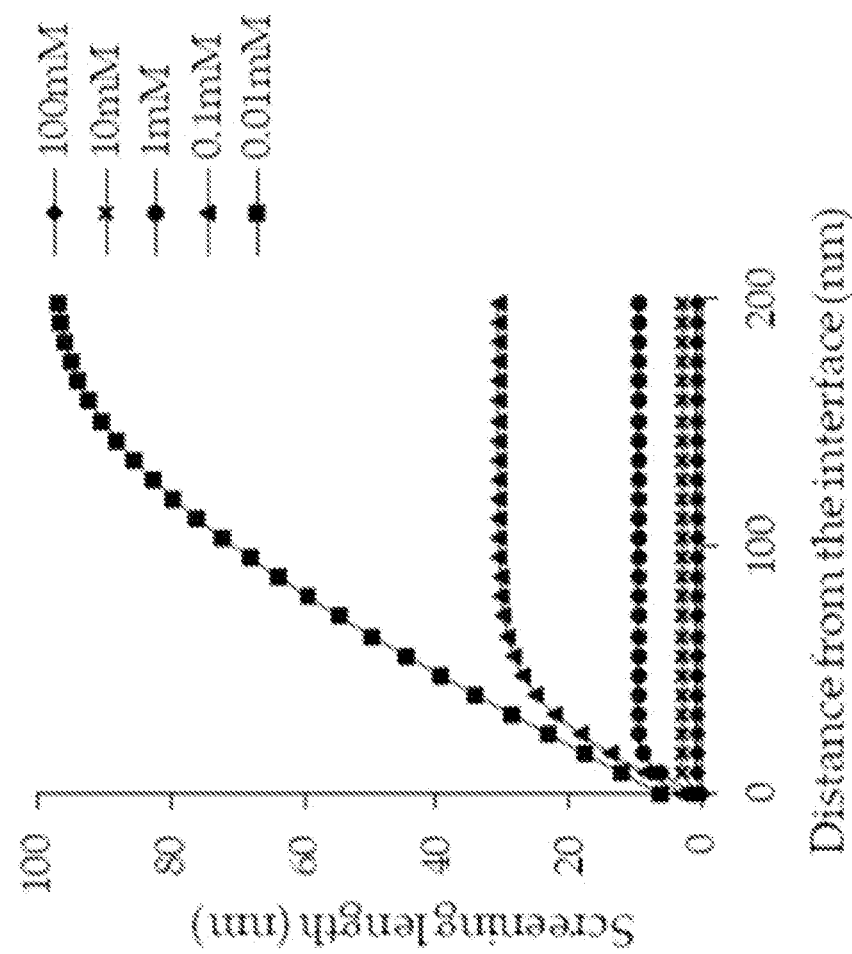
FIG. 3e depicts a numerically calculated variation of the Debye length for different ionic concentrations in an electrolyte, relative to the distance from the EOI.

FIG. 3b shows a numerically calculated hole density and counter ion (positive ions) distributions in the system of FIG. 3a where both the back gate 116d and reference electrode 122 were grounded. FIG. 3c shows a numerically calculated electric field distribution in the system of FIG. 3a, again where both the back gate 116d and reference electrode 122 were grounded. A region 114 of high concentration of ions (in the order of $10^{19}/cm^{-3}$) at the interface between the solution and the gateox 116a can be seen in FIG. 3b. Similarly, a region 124 of a high electric field can be seen in FIG. 3c at the interface between the solution and the gateox 116a. The deficiencies associated with this high concentration of ions have been discussed above. FIG. 3d shows numerically calculated variation of the electric field in the electrolyte solution 120 for different ionic concentrations relative to the distance from the electrolyte-oxide interface (EOI) and towards the bulk solution. The upper graphs depict the hole/counter-ion density, while the lower graphs depict the electric field. Finally, FIG. 3e depicts the numerically calculated variation of the Debye length for different ionic concentrations in the electrolyte (namely, the solution 120), relative to the distance from the EOI towards the bulk solution. It can be seen that the Debye length $\lambda_D$ significantly drops at or in the proximity of the (EOI) for all the various ionic strength, (in mMolar units). The small Debye length $\lambda_D$ in the proximity of the gateox 116a prevents sensing measurements from taking place as the target molecules are electrostatically screened.

Figure 4A:
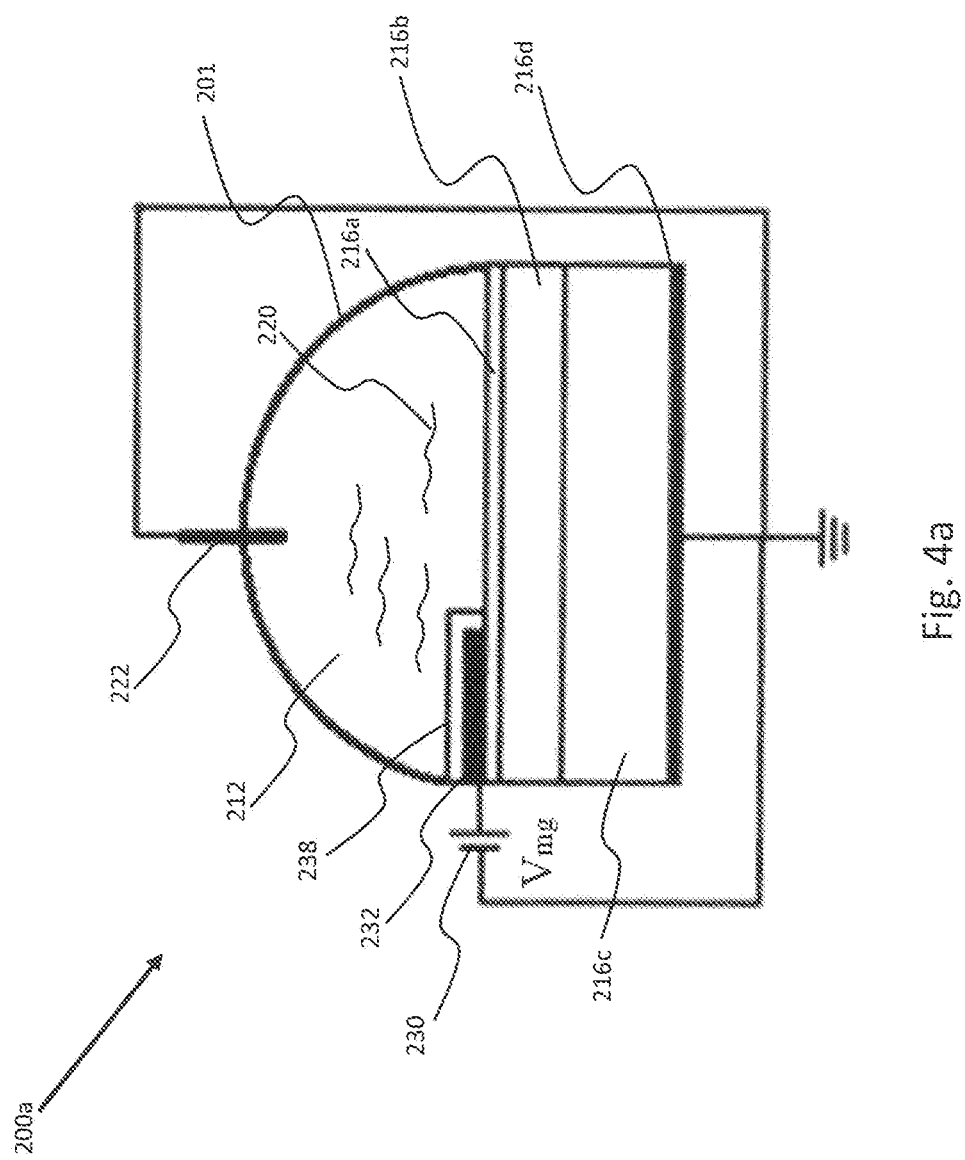
FIG. 4a shows a basic structure of a lab-on-chip system, as was used in numerical calculations.
Figure 4B:
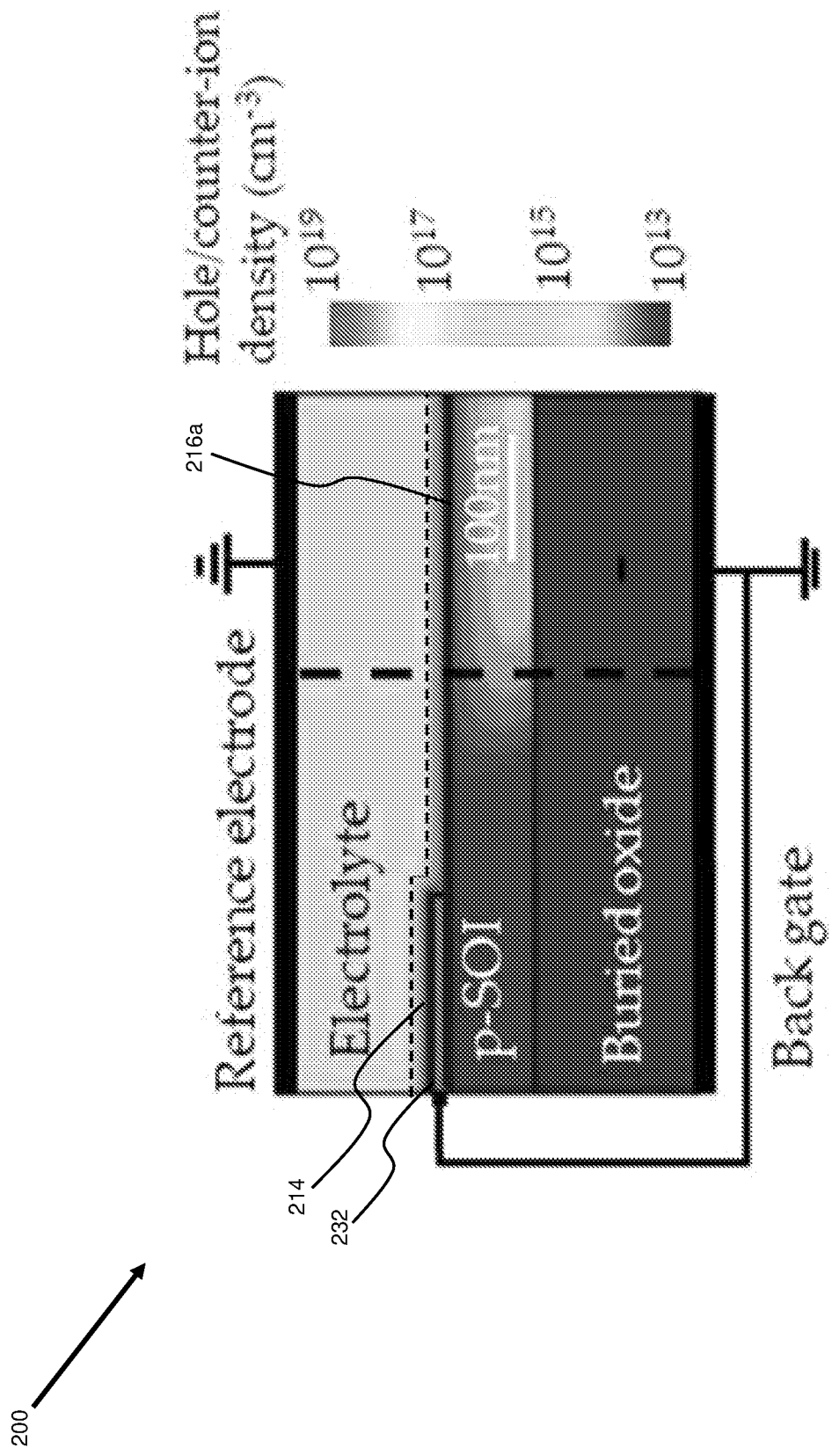
Figure 4C:
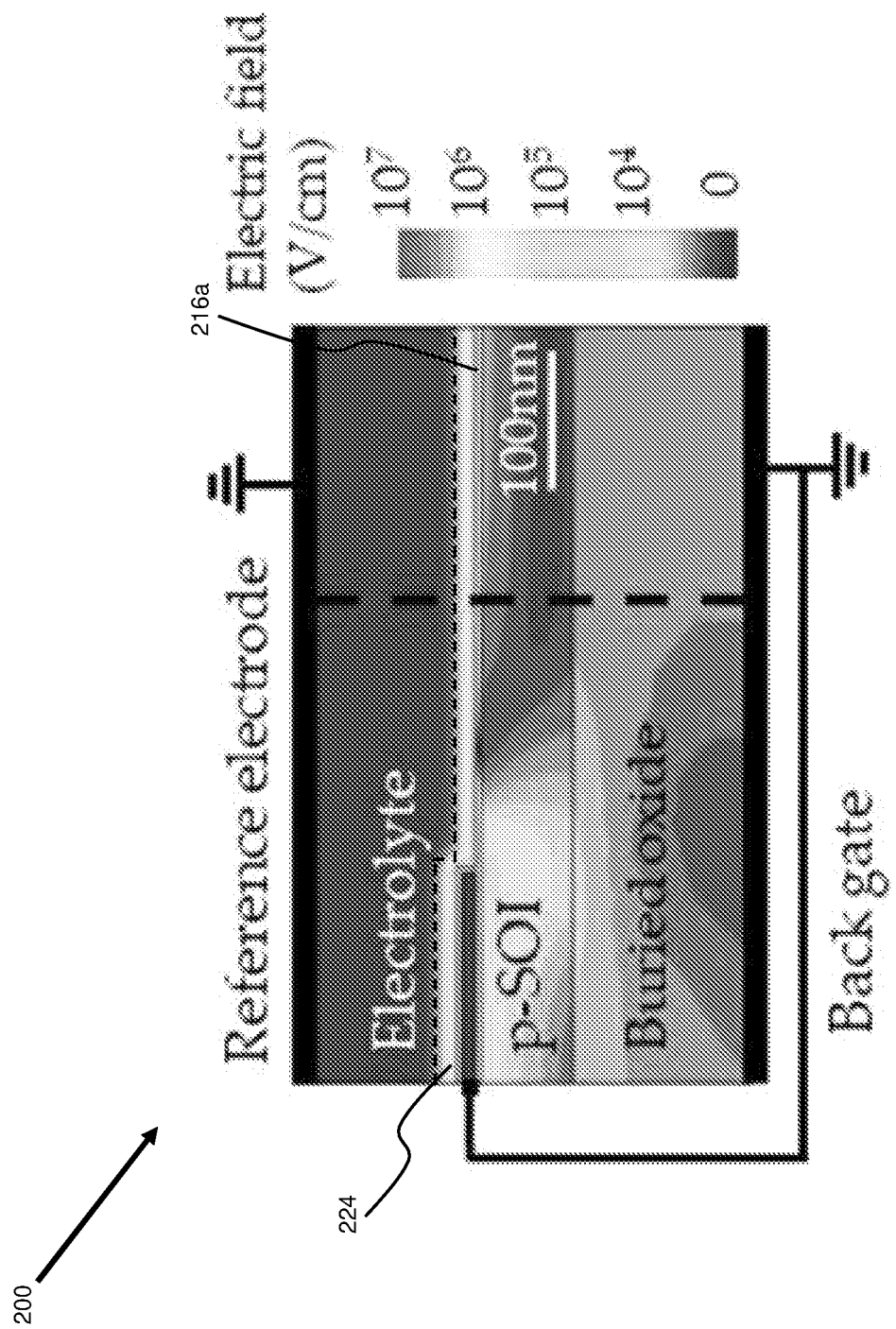

FIG. 4a shows the lab-on-chip system 200a of the invention that was further used during the numerical calculations. The lab-on-chip system 200a, including the voltage that was provided, is identical to the system 200 of FIG. 2, however, without specifically indicating the sensing layer 218 (that was included in the structure of FIG. 2). The effect of the biological interaction between the sensing layer and the target molecules was treated as an induced EOI surface charge. FIG. 4b shows a numerically calculated hole density distribution in the structure of FIG. 4a, however, for the sake of comparison only, in this specific case the back gate 216d, the reference electrode 222, as well as the metal-gate electrode 232 are all grounded. FIG. 4c shows a numerically calculated electric field distribution in the system of FIG. 4a, again, however, for the sake of comparison only, the back gate 216d, the reference electrode 222, as well as the metal-gate electrode 232 are all grounded. A region 214 of high concentration of ions (in the order of $10^{19}/cm^{-3}$) at the interface between the solution and the gateox 216a can be seen in the arrangement of FIG. 4b, in similarity to the case of FIG. 3b. Similarly, a region 224 of a relatively high electric field (in the order of $10^4 V/cm$) can be seen in FIG. 4c at the interface between the solution and the gateox 216a. In similarity to the case of FIGS. 3a-3e, the deficiencies associated with this high concentration of ions still exist when no voltage is provided to the sensing layer via electrode 232 (or to other layers that may cause an electric field that affects the EOI).

Figure 4D:
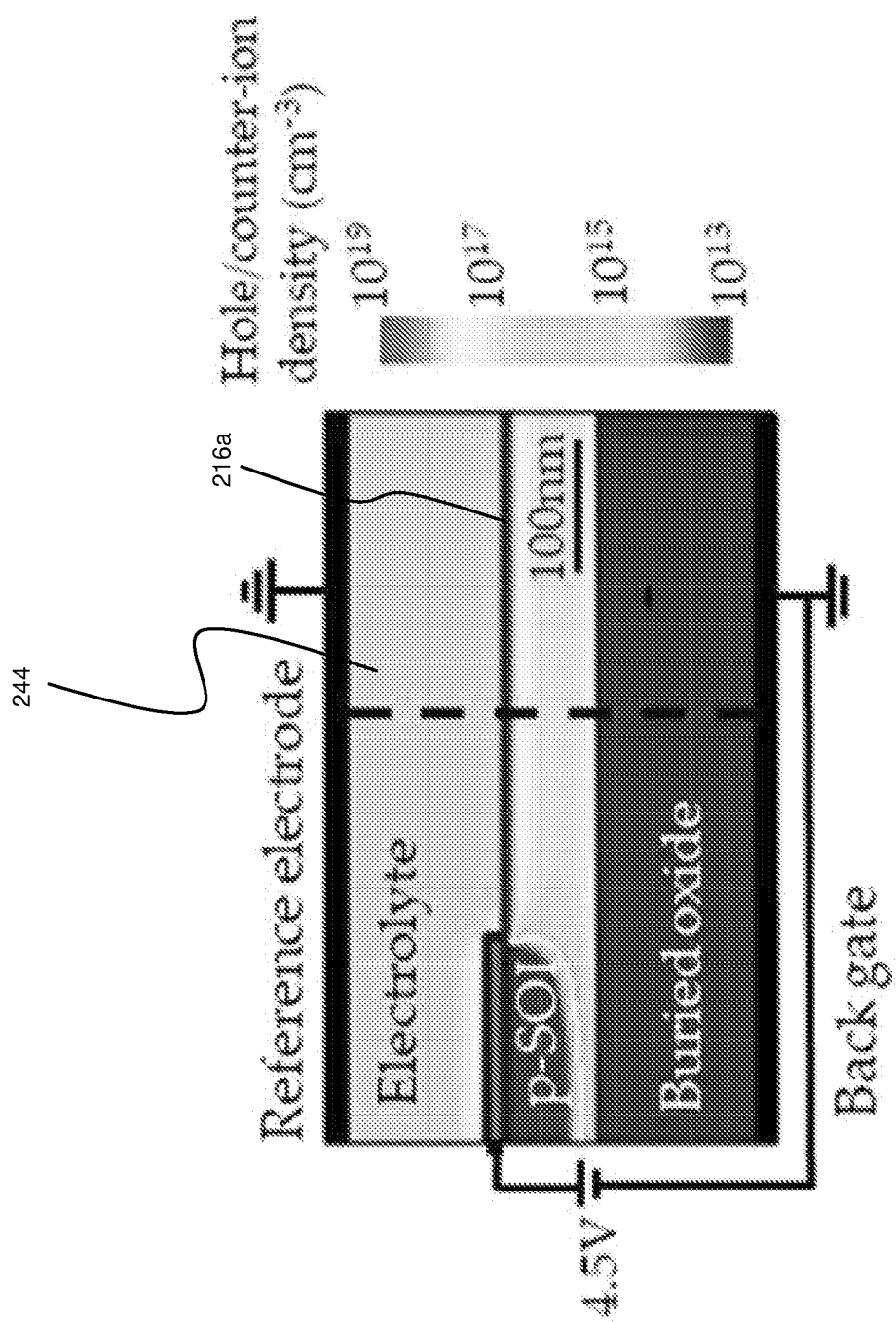
FIG. 4d shows a numerically calculated hole density and counter ion distributions in the system of FIG. 4a while a voltage of 4.5V is applied to a metal-gate electrode, and while the back gate and the reference electrode are both grounded.
Figure 4E:
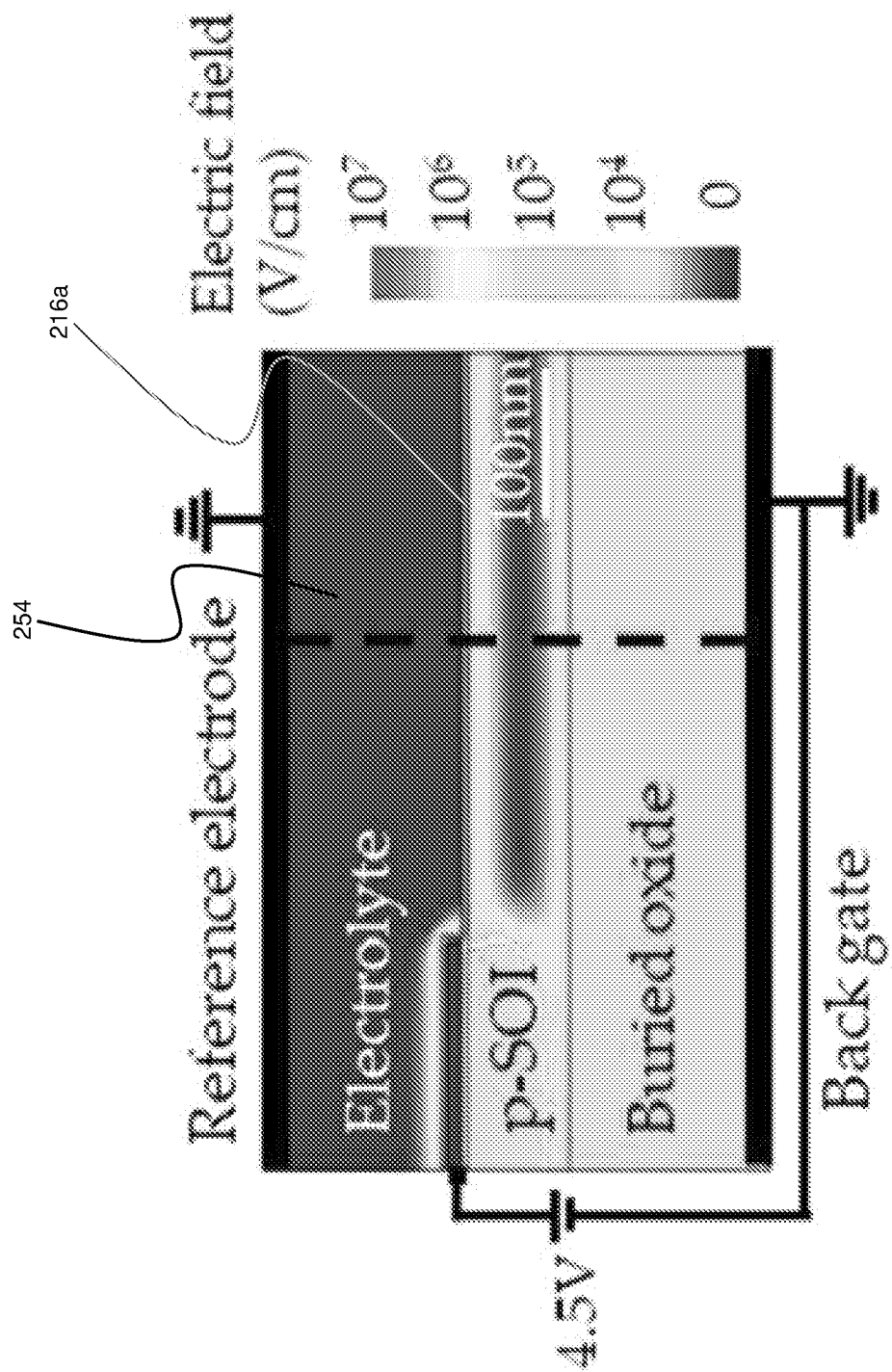
FIG. 4e shows a numerically calculated electric field distribution in the system of FIG. 4a while a voltage of 4.5V is applied to a metal-gate electrode, and while the back gate and the reference electrode are both grounded.

FIG. 4d shows a numerically calculated hole density and counter ion distributions in the system of FIG. 4a while a voltage of 4.5V is applied to the metal-gate electrode 232, and while the back gate 216d and the reference electrode 222 are both grounded. Similarly, FIG. 4e shows a numerically calculated electric field distribution in the system of FIG. 4a while a voltage of 4.5V is applied to the metal-gate electrode 232, and while the back gate 216d and the reference electrode 222 are both grounded. The region 214 of high concentration of ions, as appeared in the arrangement of FIG. 4b has been disappeared and does not exist in the arrangement of FIG. 4d. On the contrary, it can be seen that the concentration of ions 244 throughout the entire volume of the solution (electrolyte), including the interface with the gateox 216a, is homogeneously low in the arrangement of FIG. 4d (in this example in the order of $10^{17}/cm^{-3}$). Similarly, it can be seen in FIG. 4e that the region 224 of a relatively strong electric field (in the order of $10^4 V/cm$) that appeared in the arrangement of FIG. 4c has been disappeared. Moreover, it can be seen that the electric field 254 throughout the entire volume of the solution and the interface with the sensing layer is homogeneously low (practically 0V/cm). Therefore, all the deficiencies associated with the high concentration of ions at the solution-sensing layer have been eliminated by this structure.

In the embodiment of FIG. 2, the one or more isolated electrodes 232 were positioned on the sensing layer. This location of the isolated electrodes is not mandatory, as applying of voltage to the sensing layer, or more specifically, the provision of an electric field to the EOI can be made in various other manners. For example, the metal-gate electrode 232 may alternatively be positioned on top of the gateox 216a. In another embodiment, discussed in more detail with respect to FIGS. 5a-5c, the one or more isolated electrodes may be in the form of P-N junctions, that are embedded within the SOI layer. The one or more electrodes (either in the form of a metal electrode or in the form of a P-N junction) may be positioned either remote or close to the active area where the interaction with the solution molecules takes place (as long as the electric field is strong enough to affect the EOI interface).

Figure 5A:
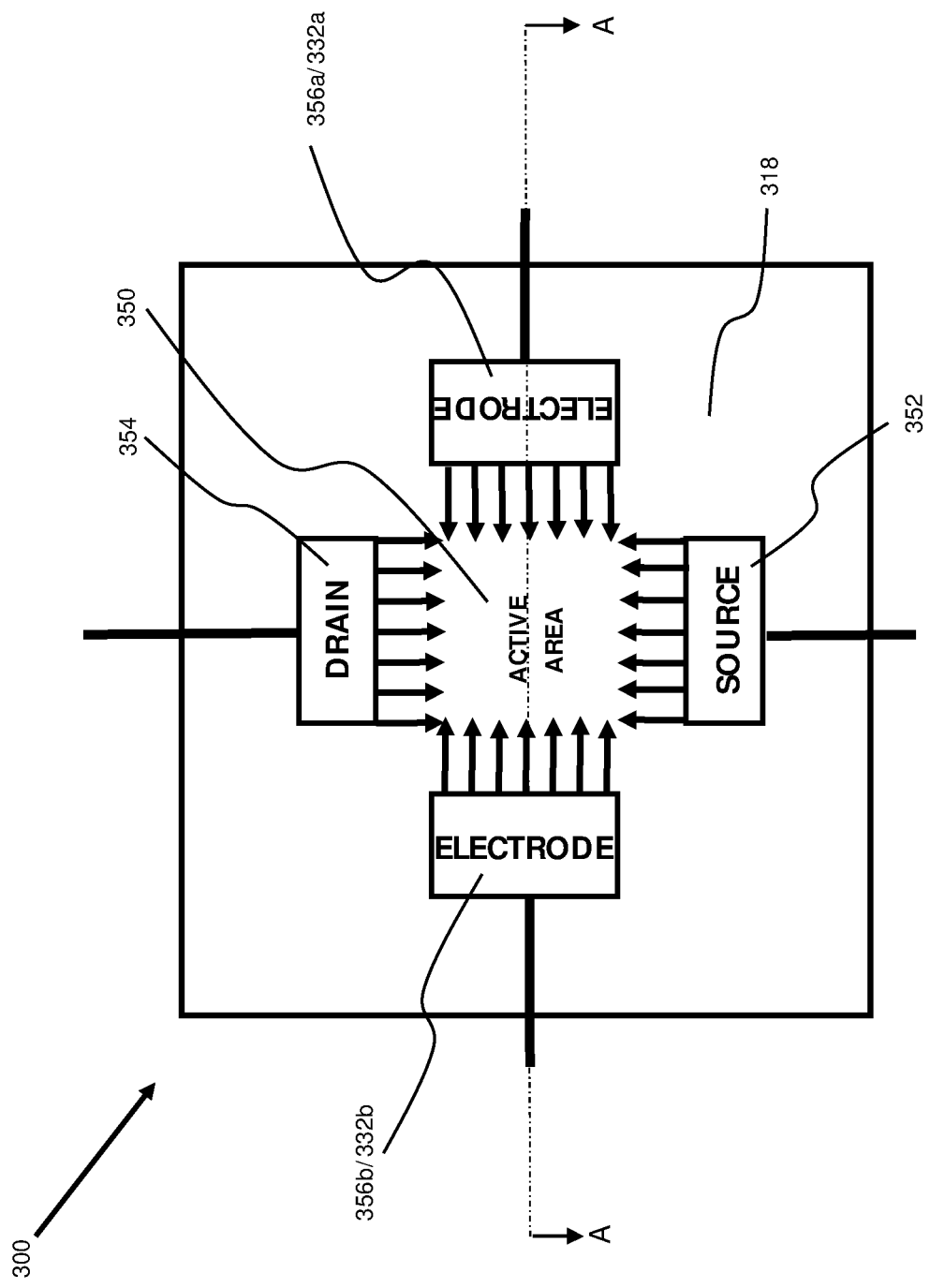
FIG. 5a shows a schematic top view of a biosensor according to an embodiment of the invention.
Figures 1, 5B:
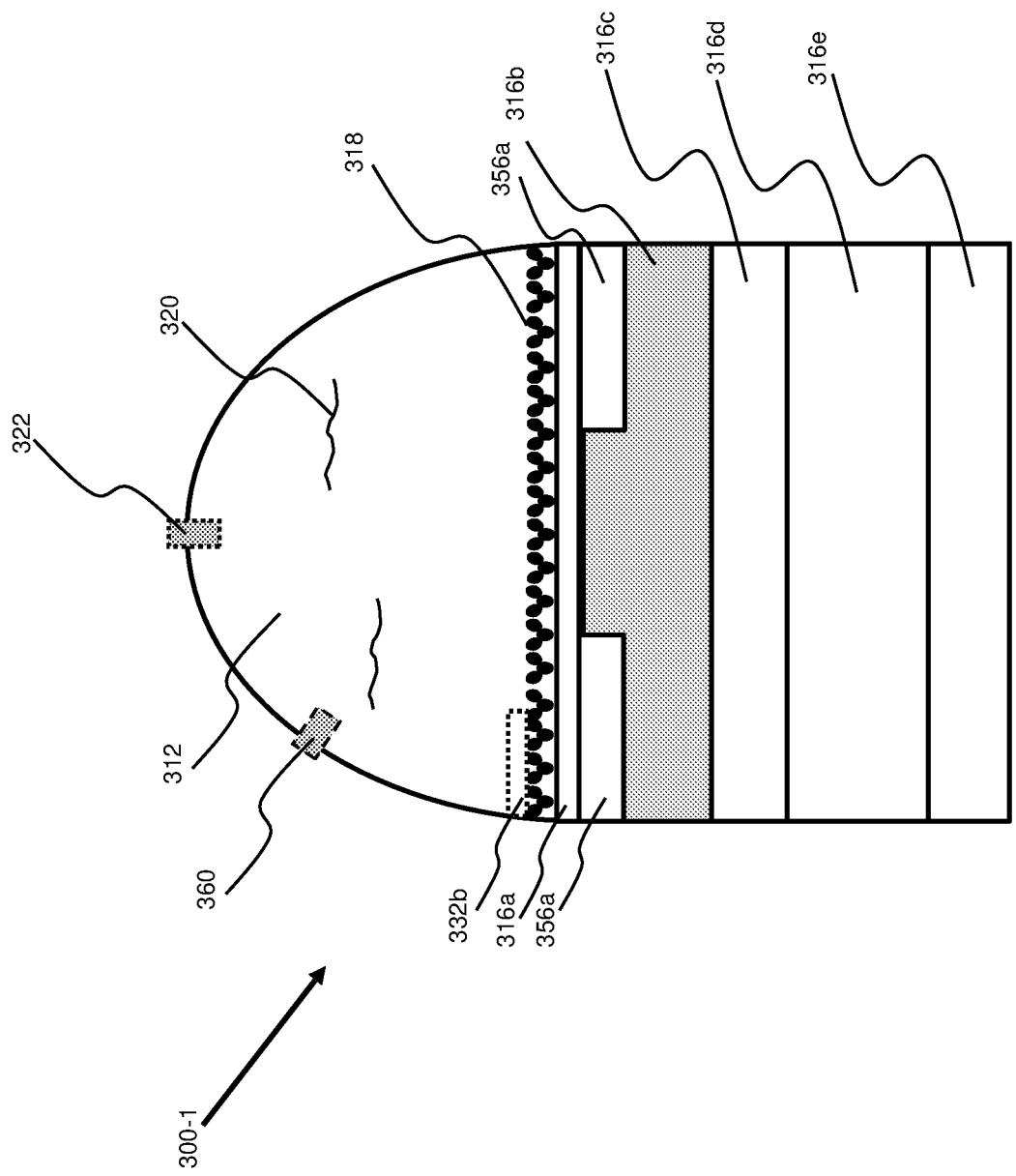
Figures 2, 5B:
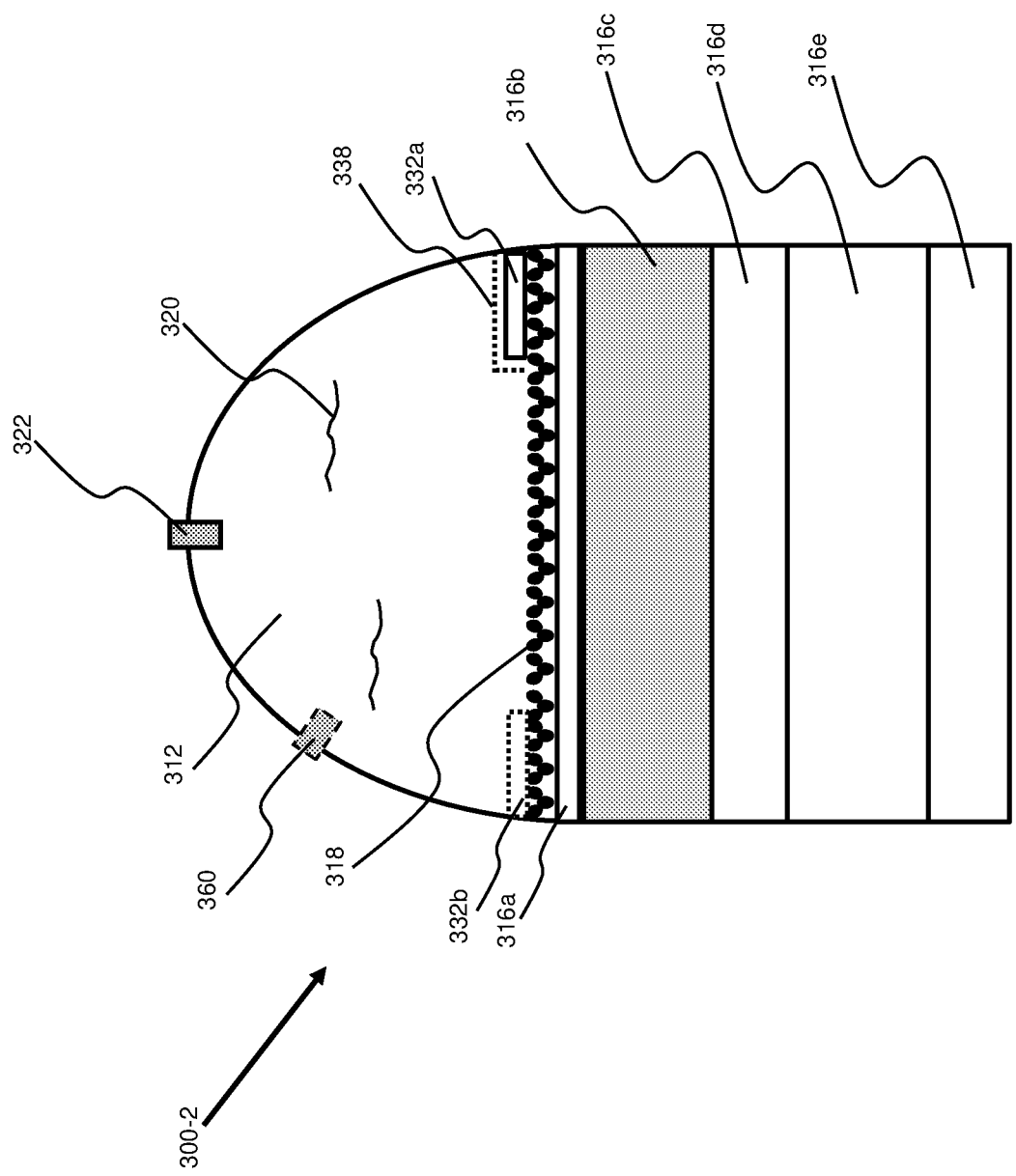
Figures 3, 5B:
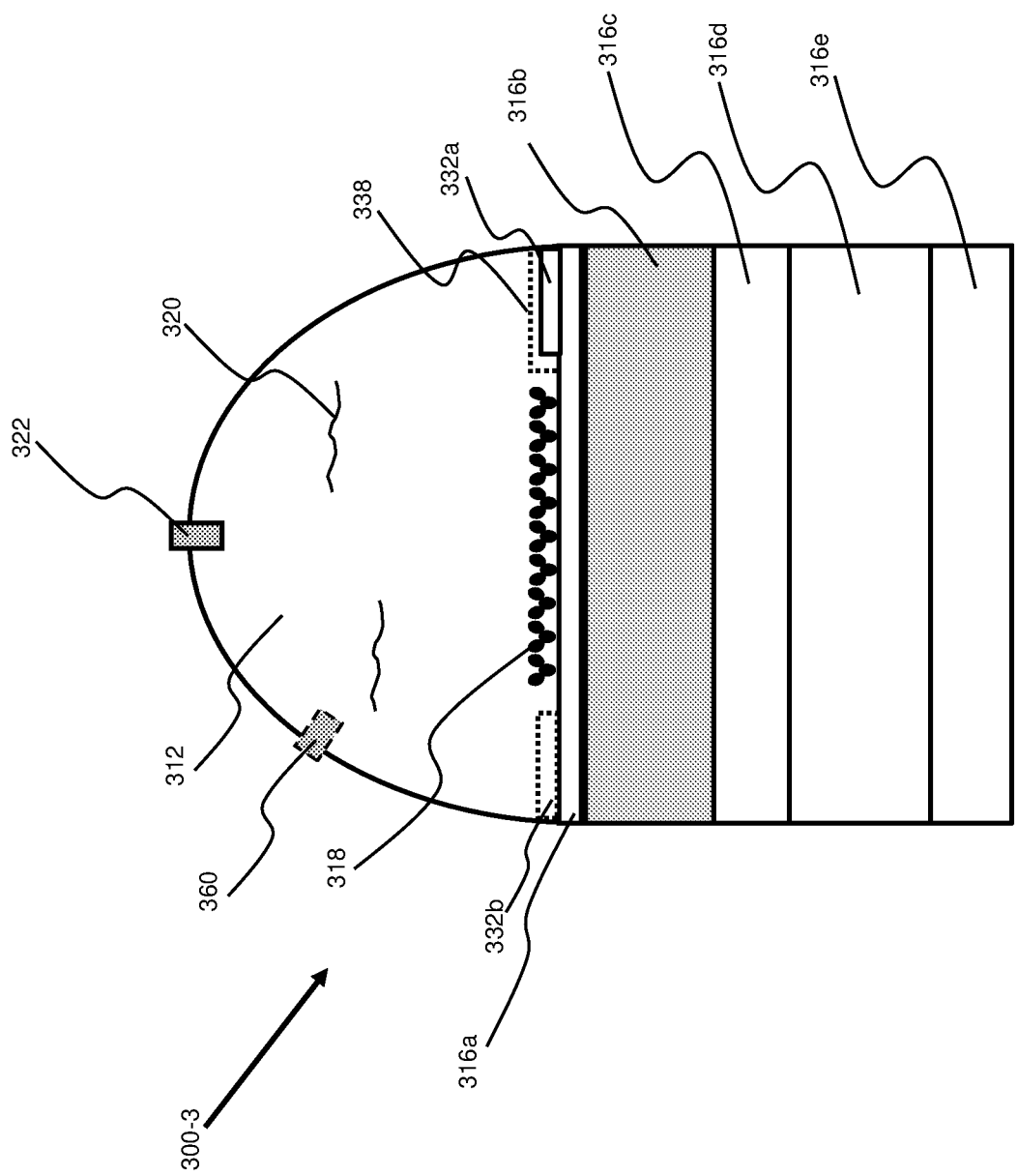
Figure 5C:
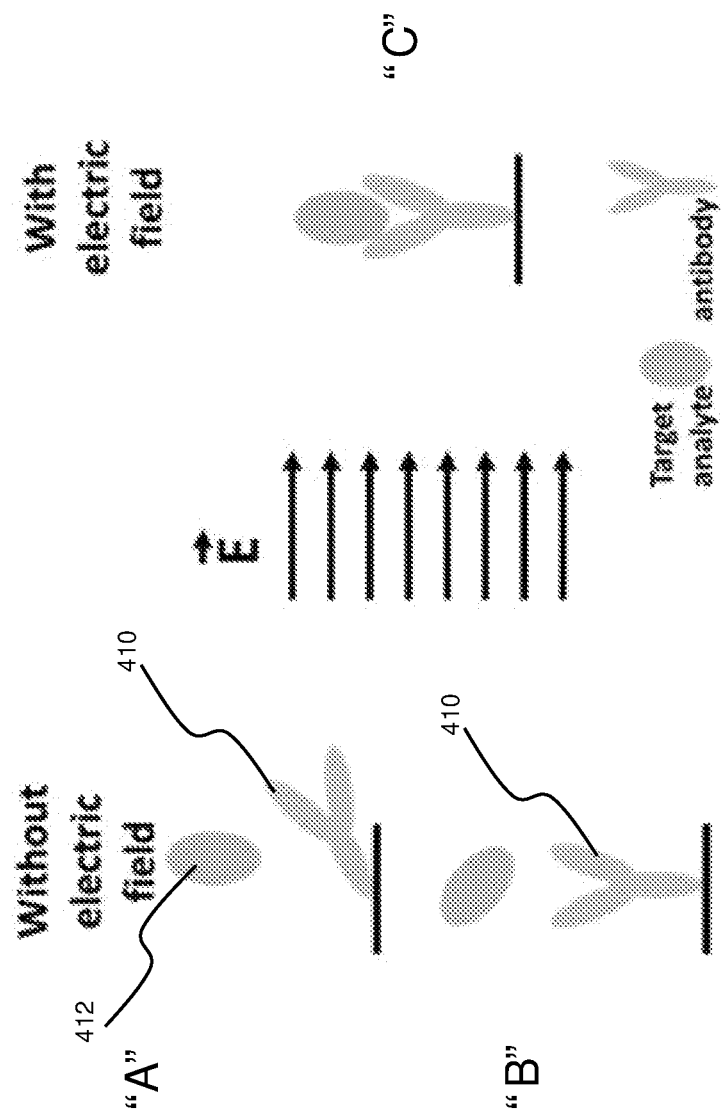
FIG. 5c illustrates how the invention improves the capturing of target molecules by receptors at the sensing layer in the device of the present invention.

FIGS. 5a to 5c show additional embodiments of the lab-on-chip biosensor of the invention. These figures are principle and schematic, particularly in terms of dimensions. FIG. 5a shows a schematic top view of biosensor 300. FIGS. 5b-1 to 5b-3 show a cross-sectional view of the biosensor of FIG. 5a, however with 3 different structural possibilities. In similarity to device 200 of FIG. 2, device 300 includes a solution compartment 312, a sensing layer 318, and a readout structure 316. The solution, for example, is electrolyte 320. In this specific example, the sensing layer 318 includes receptor molecules for a specific or non-specific interaction with target molecules in the solution. Various readout structures may be used in conjunction with the biosensor of the invention, such as an SOI structure, one or more transistors, one or more bulk-transistors, any semiconductor material, electrochemical impedance spectroscopy, capacitance-voltage (CV), measurements, etc. In the specific example of FIGS. 5a to 5c an SOI structure is used for the readout module 316. The readout-SOI structure includes a gateox 316a, an SOI (p-type or n-type silicon) layer 316b, an isolating buried-oxide ("box") layer 316c, a handle layer 316d which provides mechanical strength, and a back gate layer 316e. Optional reference electrode 322 and one or more optional counter electrodes 360 may be provided at the cover of the solution compartment 312 and are configured to be in contact with the solution 320. The optional reference electrode 322 (if exists), as well as the optional counter electrode and back gate 316e, grounded during operation. One or more isolated electrodes 356a/33a are provided at the biosensor for the creation of an electric field at the EOI interface and to affect its behavior. The index 356a refers to an electrode in a form of, for example, a p-n junction realized at the surface of the bulk silicon wafer, and electrode 332a is an electrode that is deposited on the sensing layer or the gateox. One or more optional non-isolated electrodes 356b/332b may be provided to allow ion current flow through the solution 312. This surface ion current will affect the biological interaction either during the introduction of the target molecules or during readout. Additional electrodes, such as source 352 and drain 354 are provided at the readout module, for outputting the sensed signal (however, they are not shown in FIGS. 3b-1, 3b-2, and 3b-3).

FIGS. 5b-1 to 5b-3 illustrate three possible structures of biosensor 300 in a cross-section view which is made along line A-A of FIG. 5a. The biosensor 300-1 of FIG. 5b-1 includes a sensing layer 318 on top of gateox 316a, and two isolated P-N electrodes 356a that are embedded within the SOI layer 316b. Biosensor 300-1, in this embodiment, requires at least one of such isolated electrode 356a. The sensing layer 318 may include receptors that are designed to capture target molecules from solution 312. A provision of voltage to the one or more isolated electrodes 356a causes an electric field that affects the electrostatics in the region which surrounds the electrodes, including the EOI. One or more optional non-isolated electrodes 332b may be provided on top of the sensing layer or the gateox 316a, in addition to the one or more isolated electrodes 356a that are embedded within the SOI layer. Upon provision of voltage to electrodes 332b, ion-current flows from each respective electrode through the solution 312 and towards one or more of other isolated electrodes 332b, or towards reference or counter electrodes 322 or 360. The fact that the current exerts force affects the orientation of the biomolecules (receptors and targets) at the proximity of the EOI/Double Layer, or in the bulk solution on the sensing layer 318, and thereby increases the probability of them to collect target molecules from the solution 312. Alternatively, a surface ion current will supply or remove solution ions and in this manner will affect the biological interaction. A proper design of the location of the non-isolated electrodes 332b, and the location of reference and counter electrodes 322 and 360, respectively, as well as the voltage which is provided to them, can improve and optimize the probability of capturing of target molecules by the receptors. This optimization will assist in analyzing the solution's ingredients. The readout structure may measure the effect of the ion current on the receptors and solution molecules to facilitate a means to govern molecular interactions at the close vicinity of the sensing layer, for example, target-receptor interaction.

As mentioned before, the electric field which is created eliminates the inherent concentration of ions at the interface between the solution 220 and the sensing layer 218. This elimination of ions resolves all the three problems mentioned above, namely: (a) It eliminates the Debye screening region of non-sensing, by very significantly increasing the $\lambda_D$; (b) It eliminates the high electric fields at the sensing area which is in contrast with the trivial electric fields at the solution's bulk; and, (c) It causes the pH of the solution at the interface to be the same as in the main mass of the solution, and (d) it provides surface ion concentration identical to the ion concentration in the bulk solution.

The biosensor of the invention is an active device, as it both affects the solution and the sensing layer, and then it measures this effect. This is in contrast to prior art biosensors that are passive, as they do not affect the solution either before or during the measurement. In some embodiments, the operation may include two separate stages.

In the first stage, the electric field, possibly currents through the solution are provided, and in the second stage, the effect of the electric field and/or current is measured. In this form of operation, and while operating with the embodiment 300-1, the source and drain electrodes 352 and 354, respectively, that are not used in the first stage may be used as isolated electrodes (in similarity to the function of electrodes embedded electrodes 356a).

FIG. 5b-2 shows another embodiment of the invention. The biosensor 300-2 includes a sensing layer 318 on top of gateox 316a, and one (or more) isolated electrodes 332a (having isolation 338) that are positioned on top of the sensing layer 318. Again, biosensor 300-2 requires at least one of such isolated electrode 332a. Again, the sensing layer 318 may include receptors that are designed to capture target molecules from solution 312. A provision of voltage to the one or more isolated electrodes 332a causes an electric field that affects the region which surrounds the electrodes, including the EOI. One or more optional non-isolated electrodes 332b may be provided on top of the sensing layer or the gateox 316a, in addition to the one or more isolated electrodes 332a. Upon provision of voltage to electrodes 332b, ion-current flows from each respective electrode through the solution 312 and towards one or more of other non-isolated electrodes 332b, or towards reference or counter electrodes 322 or 360. The operation and the respective effects of biosensor 300-2 are substantially the same as of the operation and effects of biosensor 300-1, therefore the explanation will not be repeated further for the sake of brevity.

FIG. 5b-3 shows still another embodiment of the invention. The biosensor 300-3 includes a sensing layer 318 on top of a section of gateox 316a (the "active area" 350 of FIG. 5a), and one (or more) isolated electrodes 332a that are positioned on top of gateox 316a. Again, biosensor 300-3 requires at least one of such isolated electrode 332a. Again, the sensing layer 318 may include receptors that are designed to capture target molecules from solution 312. A provision of voltage to the one or more isolated electrodes 332a causes an electric field that affects the region which surrounds the electrodes, including the EOI. One or more optional non-isolated electrodes 332b may be provided on top of the gateox 316a (or sensing layer 318), in addition to the one or more isolated electrodes 332a. Upon provision of voltage to electrodes 332b, ion-current flows from each respective electrode through the solution 312 and towards one or more of other non-isolated electrodes 332b, or towards reference or counter electrodes 322 or 360. The operation and the respective effects of biosensor 300-3 are substantially the same as of the operation and effects of biosensors 300-1 and 300-2, therefore the explanation will not be repeated further for the sake of brevity.

1. The structure of biosensor 300 may vary to include any combination of biosensors 300-1 to 300-3. In all the alternatives, either AC or DC voltage may be provided to the isolated or non-isolated electrodes. The application of AC voltage, for example, could induce the biological system or the solution ions into resonance and/or arrange the solution ions in such a way that will affect the biological interaction. Furthermore, while the description has been specifically focused on a silicon-based structure, other alternative materials, such as organic or inorganic semiconductor or metal materials may be used in the structure. Furthermore, the readout circuit may be selected from a FET-type, capacitance-voltage measurement, or electrochemical impedance spectroscopy.

Example 1

The biosensor 300, in this specific example, is realized on a silicon-on-insulator (SOI) wafer. In similarity to embodiment 300-1, the biosensor includes four lateral electrodes, source 352 and drain 354 (that are embedded within the SOI layer 316b), and two isolated electrodes 356a that are also embedded within the SOI layer 316b. The SOI layer 316b is an n-type (or p-type) substrate and the four electrodes 352, 354, and two electrodes 356a are of opposite doping. In this manner, P-N junctions are formed between the four lateral electrodes and the SOI layer 316b. When a bias is provided to one or more of electrodes 356a, a formation of p-n junction generates an electric field in the depletion regions. The strength of the electric fields depends on both the doping and the biasing of the junctions. The active area 350 is a location where a bio-recognition event takes place. As noted, in one example the active area 350, within the sensing layer 318 is modified to include antibodies.

As shown in FIG. 5c ("A"), the antibodies 410 within the sensing layer, as well as the target molecules 412 within the solution 320 (FIG. 5b-1) are generally arranged in a random order, a situation which is not optimal for the antibodies to "capture" the target molecules. A better situation is shown in FIG. 5c ("B") where the antibodies 410 are directed upwards towards the target molecules. An optimal situation is shown in FIG. 5c "C" where both the antibody and the target molecules are vertically oriented. The application of voltage to the one or more non-isolated electrodes 332 of bio-sensor 300 causes an electric field E that in turn causes the antibodies and/or the target molecules to be vertically oriented, as in "C". In this manner, the probability to capture target molecules significantly increases. A similar effect can be achieved by using non-isolated electrodes and surface ion current.

It should be noted that biological molecules within the solution carry either a net electric charge or an electric dipole. Therefore, the local fringing electric field performs work on such molecules, as demonstrated in FIG. 5c "C". FIG. 5c illustrates a bio-recognition process in the presence of electric fields. "A" and "B": without an electric field. "C": with an electric field. The induced local fringing electric fields affect the orientation of both the target molecule and the antibody to be vertically directed. The induced local electric fringing field affects the biological event. These fields can align the molecules in such a manner that provides a spatial orientation of the molecules and increases the probability for interaction, and hence the sensitivity, the response, and the dynamic range of the biosensor.

The source electrode 352 and the drain electrode 354 perform the actual transduction of the variation of surface potential that was induced by the biological event to a significant variation in current. The doping and thickness of the SOI ensure that the SOI is fully depleted. During the transduction, two of the four lateral electrodes may take the role of source and drain. The other two electrodes may be disconnected. In fact, the device operates as a double-gate inversion-mode transistor. A correct biasing of the electrodes and the back gate ensures that the device operates with maximum sensitivity to variations in surface potential. It was found that such a device attains an optimal sub-threshold swing.

The above is only one example. Various other arrangements that form local electric fringing fields combined with a device that is highly sensitive to variations in surface potential can be formed. For example, the lab-on-chip of the invention may include one or more isolated electrodes (such as electrode 232 of FIG. 2) and one or more non-isolated electrodes (such as electrodes 356b of FIG. 5a).

Example and Theoretical Discussion

The challenge of the Debye screening length becomes much more acute at the solution-oxide interface due to the presence of surface amphoteric sites that either accept or donate protons to become positively or negatively charged respectively, resulting in a net oxide surface charge density ($\sigma_0$). To maintain charge neutrality across the interface, an equal and oppositely charged concentration of solvent ions (counter-ions relative to $\sigma_0$) is adsorbed on the EOI, leading to the formation of a DL (double layer). The local average concentrations of positive and negative ions at x distance from the EOI in the electrolyte are described by the Boltzmann distribution theorem $\rho_+ =$ $$\rho_{+,B}\exp\left(-\frac{z_+ q\Psi(x)}{kT}\right) \text{ and } \rho_- = \rho_{-,B}\exp\left(\frac{z_- q\Psi(x)}{kT}\right),$$

where $\rho_+, B$ and $\rho_-, B$ are the respective bulk concentrations, $\Psi(x)$ is the average electric potential at a distance x away from the EOI, q is the elementary charge, k is the Boltzmann constant and T is the temperature. Accordingly, the one-dimensional (1D) Poisson-Boltzmann (PB) equation for a symmetrical electrolyte ($z_+ = z_- = z$ and $\rho_+, B = \rho_{B)}$, $B = \rho_{B)}$ is $$\frac{d^2\Psi(x)}{dx^2} = \frac{8\pi\rho_B qz}{\varepsilon}\sinh\left(\frac{zq\Psi(x)}{kT}\right)$$

where $\varepsilon$ is the relative electrolyte permittivity. For EOI surface potential $\Psi_0 < kT/q$, the DL dynamics follow the Debye-Huckel approximation for which the co-ions and counter-ions concentrations depend linearly on $\Psi(x)$ and hence an excess of counter-ions entails an identical deficit of co-ions, whereas for the Gouy-Chapman (GC) regime with $\Psi_0 > kT/q$ the concentration of the counter-ions is significantly higher. The GC condition is the more important approximation for bioFETs as it is fulfilled for $\Psi_0$ values of typical oxides, such as $SiO_2$, $Al_2O_3$, $Ta_2O_5$ and others (e.g. $\Psi W_0 = 100$ mV for $SiO_2$ at pH7 and 100 mM ionic strength), for a wide range of pH levels and ionic strengths; therefore, in this case, the overall total DL ion concentration ($\rho_0$) is appreciably higher than $\rho_B$. Alternatively, integration of the 1D PB equation for both symmetric and asymmetric electrolyte yields the Grahame equation which describes the relation between $\rho_0$ and $\sigma_0$ such that $\Sigma_i\rho_{0i} = \Sigma_i\rho_{Bi} + 2\pi\sigma_0^2/\varepsilon kT$, where the sum extends over all ion species i; the Grahame equation shows that $\rho_0$ will always be greater than $\sigma_B$ and the excess concentration depends only on $\sigma_0$.

The PB equation considers only electrostatic interactions and various other studies considered other contributions to the DL dynamics such as the Steric effects, dielectric decrement, ion-ion correlation in which all yielded $\rho_0 \gg \rho_B$. As a corollary, the potential decay profile and the DL total ion concentration which are characterized by $\lambda_D$ corresponding to the local ion concentration also becomes independent of $\rho_B$ in the proximity of the interface and the excess of ions causes the screening length near the interface to be much smaller than $\lambda_D$. Thus, for any ionic concentration, the maximum screening takes place at the EOI and gradually decreases towards the bulk.

The invention introduces a new approach to electrostatically govern the EOI using local tunable surface electric fields. The inventors examined how the application of the electrical fields affects the mobile charge distributions on both sides of the gate oxide (as noted, the numerical calculations assumed that a sensing layer exists), and how flat-band conditions are established at the double layer (DL). Finally, The inventors used the suggested paradigm to demonstrate enhanced field-effect based biosensing.

Three-dimensional electrical-device calculations were performed using Advanced TCAD by Synopsys (Mountain View, CA, USA). The Poisson and continuity equations were solved for each mesh vertex while doping-dependent mobility was considered.

A 1:1 ratio electrolyte was modeled as an intrinsic semiconductor with energy gap $E_g = 1.5$ eV such that $(E_g/2 - q\Psi) \gg kT$ was satisfied to reduce Fermi statistics in semiconductors to Boltzmann statistics in electrolytes. The permittivity of the semiconductor was set to 80 to reproduce the behavior of water. The hole (p) and electron (n) concentrations of the intrinsic semiconductor were adjusted to mimic the positive and negative ion concentrations calculated as: $p = n = N_{Av} c_0 \times 10^{-3}$ cm$^{-3}$ where $c_0$ is the ionic strength of the solution. The effective density of states of conduction ($N_c$) and valence ($N_v$) bands were calculated as $N_c = N_v = ne^{E_g/2kT} = pe^{E_g/2kT}$. The maximum mobility values of the holes and electrons were set to $\mu_p^{max} 4.98 \times 10^{-4}$ CM$^2$V$^{-1}$s$^{-1}$ and $\mu_n^{max} = 6.88 \times 10^{-4}$ cm$^2$V$^{-1}$x$^{-1}$ respectively to replicate the behavior of Na$^+$ and Cl$^-$ ions in NaCl solution. The surface potential $\Psi_0$ at pH=7 and dissociation constants for gate oxide materials are taken from literature and the corresponding $$\sigma_0 = qN_s\left(\frac{a_{H_s^+}^2 - K_a K_b}{K_a K_b + K_b a_{H_s^+} - a_{H_s^+}^2}\right)$$

where $N_s$ is the fixed number of surface sites per unit area, $\alpha_{H_s^+}^2$ is the surface proton activity and $K_a$ and $K_b$ are the surface dissociation constants.

In brief: FIG. 3a is a schematic illustration of the electrolyte-oxide-silicon (EIS) system where the EOI, front interface, and back interface have been indicated. FIG. 3b shows a numerically calculated hole density distribution in the EIS system when both the back gate and reference electrode are grounded. FIG. 3c shows a numerically calculated electric field distribution in the EIS system when both the back gate and reference electrode are grounded. FIG. 3d shows numerically calculated variation of the electric field in the electrolyte for different ionic concentrations with distance from the EOI towards the bulk. FIG. 3e shows numerically calculated variation of the Debye length for different ionic concentrations of the electrolyte with distance from the interface towards the bulk.

FIG. 3a presents an illustration of an electrolyte-insulator-semiconductor (EIS) system realized on a fully-depleted (FD) silicon-on-insulator (SOI)—the electrical electrodes of the back gate ($V_{Gb}$) and the reference electrode ($V_{ref}$) are shown. The SOI layer is fully depleted for $t_{si} < kW_{max}$ for $1 < k < 2$ where $t_{si}$ is the silicon thickness and $W_{max}$ is the maximum depletion width. Importantly, the biasing of the electrolyte-insulator-semiconductor system is made possible only due to the FD-SOI that electrostatically couples the front interface with the back interface. A 100 nm p-type SOI active layer with boron doping of $1\times10^{16}$ cm$^{-3}$ on top of a 200 nm buried oxide (BOX) layer was considered. The thickness of the SiO$_2$ gate oxide, henceforth the insulator part of the EIS (referred to herein as "gateox") is 6 nm. The system mainly includes three interfaces: the BOX/SOI interface ("back interface"), the SOI/gateox interface ("front interface") and the gateox/solution interface ("EOI"). A 1:1 electrolyte of ionic strength 1 mM was considered unless otherwise stated, which yields $\sigma_0=-1.4\times10^{13}$ q cm$^{-2}$ for SiO$_2$ gateox at pH7.

To enforce the requirement for charge neutrality at the EOI, the prior art has proposed that $\sigma_0$ is balanced by an equal and opposite charge density $\sigma_{d1}$ in the DL such that:

$$\sigma_{d1} = -\sigma_0 = -C_{d1}\Psi_0 \quad (1)$$

where $C_{d1}$ is the integral double-layer capacitance. FIGS. 3b-3e present numerically calculated results. FIG. 3b presents the distribution of the solution counter-ion concentration and the hole density (p) in the SOI for the EIS system of FIG. 3a for $V_{Gb}=V_{ref}=0V$. It can be noted that the surface counter-ion concentration ($\rho_{+,0}$) is higher than the solution bulk value $\rho_{+,B}$ which reflects the formation of $\sigma_{d1}$ to compensate for the negative $\sigma_0$. It can also be noted that the SOI front interface is accumulated with p at the front interface higher than the p SOI bulk value. Therefore, $\sigma_0$ is electrically neutralized by contributions from both $\sigma_{+,0}$ and p. FIG. 3c presents the respective distribution of the electric fields that are non-trivial (not zero), ~$10^5$ Vcm$^{-1}$ at the close vicinity of the gateox due to the excess of positive charges, in contrast to the quasi-neutral regions of the bulk solution and bulk SOI. FIG. 3d presents the dependency of the DL electric field distribution on the solution ionic strength ($c_0$), where, as expected, higher ionic strength implies shorter DL and faster convergence of $\sigma_+$ and electric fields into the corresponding bulk values. The important implication of $\rho_{+,0}$ relative to $\rho_{+,B}$ is that effectively the surface screening length ($\lambda_{sc}$) is smaller at the DL compared to $\lambda_D$. FIG. 3e shows the dependency of $\lambda_{sc}$ on the distance from the EOI and on the ionic strength. Obviously, $\lambda_{sc}$ is an averaged macroscopic quantity, but still, the curves well reflect the variation between $\lambda_{sc}$ and $\lambda_D$. Note, for example, for $c_0=0.01$ mM, $\lambda_D=\sim100$ nm while at proximity to the EOI $\lambda_{sc}<10$ nm, and for $c_0=100$ mM, $\lambda=\sim1$ nm and at the EOI drops to $\lambda_{sc}=0.3$ nm. Obviously, the extremely short $\lambda_{sc}$ excludes any possibility of biological sensing based on field-effect devices, and in-fact the challenge of $\lambda_D$ is significantly more severe than described previously by the prior art.

Considering the current case of p-type SOI, equation (1) needs to be adjusted to properly account for the charges in the silicon, i.e. accumulated front interface and contribution from charged impurities ($N_A$) such that:

$$\Psi_0 = \frac{\sigma_0}{C_{dl}} = -\left(\frac{\sigma_{dl}}{C_{dl}} + \frac{\sigma_{Si}}{C_{ox}}\right) \quad (2)$$

where $C_{ox}$ is the gateox capacitance per unit area, $\sigma_{si}$ is the total charge density per unit area in the SOI front interface which equals to:

$$\sigma_{sc} = \sigma_c + \sigma_i, \quad (3)$$

where $\sigma_c$ and $\sigma_i$ are charge density per unit area of front interface mobile charge carriers and negatively-charged impurities (acceptors) respectively such that:

$$\sigma_c = q \times \left[p_0 \exp\left(-\frac{q\Psi_f}{kT}\right) + n_0\exp\left(\frac{q\Psi_f}{kT}\right)\right] \times W_D, \quad (4)$$

$$\sigma_i = q \times N_A \times W_D, \quad (5)$$

where $p_0$ and $n_0$ are the equilibrium hole and electron densities respectively, $\Psi_f$ is the front interface potential and $W_D$ is the depletion width. It was further assumed that $p>N_A$ as $\sigma_0$ is negative, the front interface is accumulated, and also $p>>n$ since n is the minority electron density. These assumptions simplify equation (2) to:

$$\Psi_0 = \frac{\sigma_0}{C_{dl}} = -\left(\frac{\sigma_{dl}}{C_{dl}} + \frac{\sigma_c}{C_{ox}}\right) \text{ where} \quad (6)$$

$$\sigma_c = q \times p_0 \exp\left(-\frac{q\Psi_f}{kT}\right) \times W_D.$$

Equation (6) clearly describes how $\sigma_0$ is neutralized by both the SOI accumulated front interface on the silicon side and by $\rho_{+,0}$ population on the solution side. As described above, $\rho_{+,0}$ determines $\lambda_{sc}$. Clearly, if one wants to increase $\lambda_{sc}$, $\rho_{+,0}$ needs to be reduced and at the same time, the requirement for EOI charge neutrality has to be fulfilled. In principle, this can be accomplished by increasing the front interface accumulation such that it fully compensates for $\sigma_0$ and in this case $\rho_{+,0}$ attains its bulk value, the surface electric fields are nulled and $\lambda_{sc}$ is increased to its maximum physically possible value $\lambda_D$.

Figure 4F:
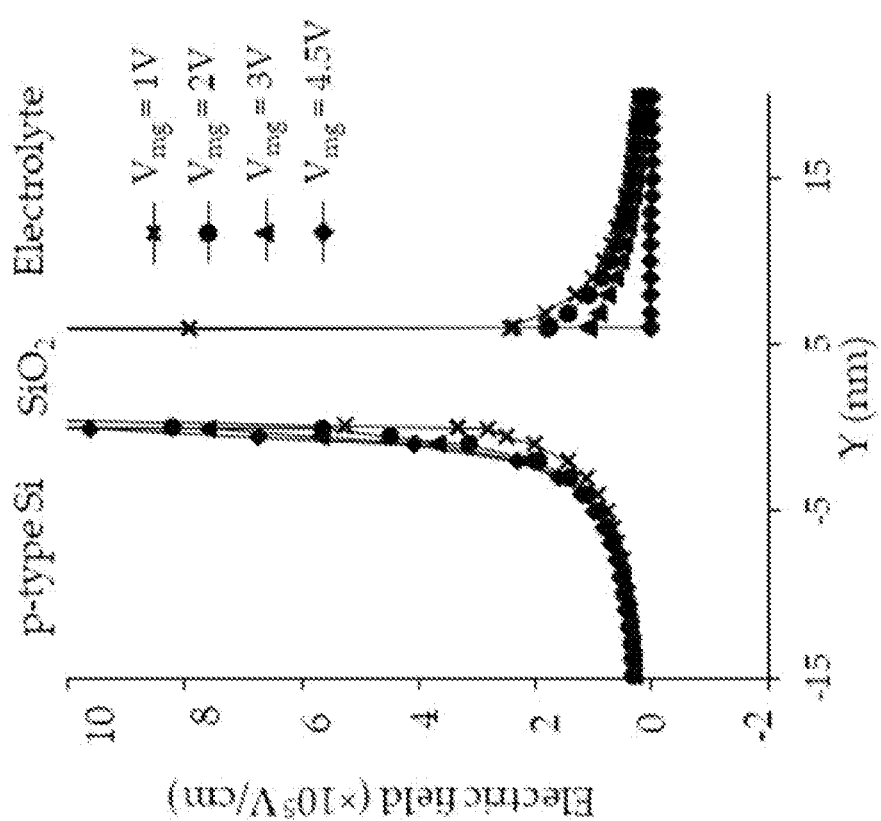
FIG. 4f shows a variation of the electric field in the silicon, the oxide layer, and the electrolyte for different $V_{mg}$ biasing voltages.
Figure 4G:
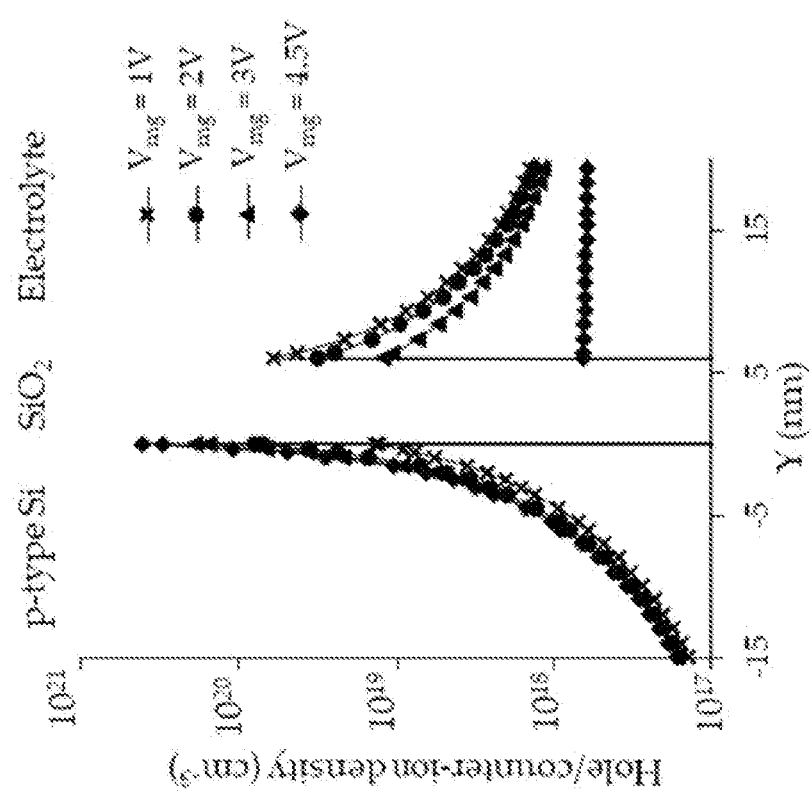
FIG. 4g shows a variation of hole density in the silicon and counter-ion concentration in the electrolyte for different $V_{mg}$ biasing voltages.
Figure 4H:
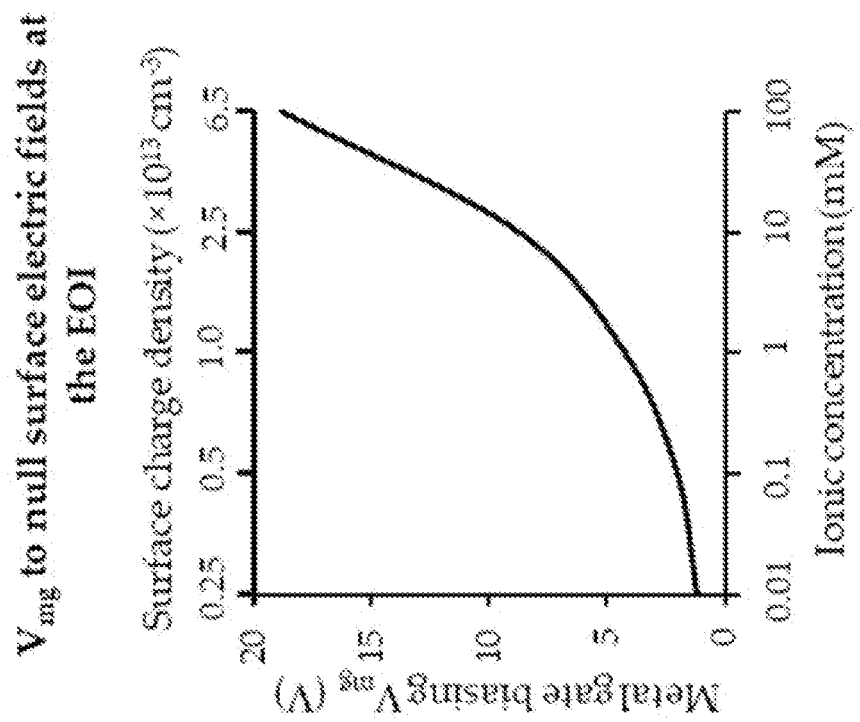
FIG. 4h shows a dependence of $V_{mg}$ on ionic strength ranging from 0.01 mM to 100 mM and their corresponding surface charge density.

In brief: FIG. 4a is a schematic representation of the electrolyte-insulator-semiconductor (EIS) system modified with a metal gate. FIGS. 4b to 4h provide numerically calculated results. FIG. 4b shows the distribution of holes and solution counter-ions in the system when all the electrodes are grounded—the vertical dotted line indicates the x-cut at which 1D data was extracted. FIG. 4c provides the electric field distribution in the system when all the electrodes are grounded—the vertical dotted line indicates the x-cut at which 1D data was extracted. FIG. 4d is the same as FIG. 3b for $V_{mg}=4.5V$. FIG. 4e is the same as FIG. 4c for $V_{mg}=4.5V$. FIG. 4f shows the variation of the electric field in the silicon, the oxide layer, and the electrolyte for different $V_{mg}$ biasing voltages. FIG. 4g shows the variation of hole density in the silicon and counter-ion concentration in the electrolyte for different $V_{mg}$ biasing voltages. FIG. 4h shows the dependence of $V_{mg}$ on ionic strength ranging from 0.01 mM to 100 mM and their corresponding surface charge density.

FIG. 4a is a schematic circuit similar to FIG. 3a, but having an additional metal electrode which is electrically and physically isolated from the solution and the SOI. In the following, the inventors demonstrate how the biasing of the metal electrode ($V_{mg}$) can be used to manipulate the charge distribution on both sides of the gateox. In essence, the $V_{mg}$ was used to directly remove excess of surface counter-ions and indirectly to preserve charge neutrality, thereby to induce a greater front interface accumulation. In this manner $\rho_{+,0}=\rho_{+,B}$ which implies that, effectively, the surface electric field at the EOI is nulled and therefore $\lambda_{sc}=\lambda_D$. In other words, correct $V_{mg}$ biasing generates a new electrostatic environment at the EOI and SOI front interface such that $\sigma_0$ is solely neutralized by the majority carriers in the SOI and the effect of $\sigma_0$ on the EOI vanishes. Hence, the biasing $V_{mg}$ modifies equation (2) to:

$$\Psi_0 = \frac{\sigma_0}{C_{dl}} = -\left(\frac{\sigma_{dl}}{C_{dl}} + \frac{\sigma_c}{C_{ox}} - V_{mg}\right) \quad (7)$$

and in order to obtain, as described above, $$\frac{\sigma_0}{C_{dl}} = -\frac{\sigma_c}{C_{ox}},$$

then the condition for $V_{mg}$ is $$V_{mg} = \frac{\sigma_{dl}}{C_{dl}}$$

which assures that the DL charge disappears, the DL obtain bulk values, $\Psi_0=0$ and $d\Psi/dx=0$ at the EOI and a flat-band condition is established at the EOI (excluding flat-band contributions from $V_{ref}$ surface dipole potential of the solution, silicon work function and fixed and interface states). Finally, the potential drop in the y-lateral direction due to $V_{mg}$ biasing is obtained directly from the PB equation $$\Psi(y) = \frac{4kT}{zq}\exp(-Ky) \text{ where } K = \sqrt{\frac{8\pi\rho_B q^2 z^2}{\varepsilon kT}}.$$

FIGS. 4b and 4c present the numerically calculated distribution of p and solution counter-ions, and the electric field distribution for $V_{mg}=V_{ref}=V_{Gb}=0V$ respectively. It can be Note the accumulation of front interface p and counter-ions at the EOI due to $\sigma_0$, and the formation of electric fields at the EOI. FIGS. 4d and 4e present the same system, however, for $V_{mg}=4.5V$ and $V_{ref}=V_{Gb}=0V$. Note how the DL counter-ion concentration is now equal to the bulk value, and the increase in front interface p reflects a further accumulation of front interface holes to neutralize $\sigma_0$. FIGS. 4f and 4g present the electric fields and the concentration distribution of holes and counter-ions respectively, throughout the front interface and EOI along the vertical dashed lines in FIGS. 4b and 4c for various biasing of $V_{mg}$ and $c_0=1$ mM. Note how the population of counter-ions and the electric fields at the EOI and DL decrease, whereas the front interface p and electric fields increase with increasing $V_{mg}$. Finally, FIG. 4h presents the $V_{mg}$ biasing values for which the EOI counter-ion concentration is equal to the bulk value ($V_{mg,\,0}$) for different $c_0$ and the corresponding value of $\sigma_0$. $V_{mg,\,0}$ has a negligible dependence on the SOI doping (not shown).

Figures 6A, 6B:
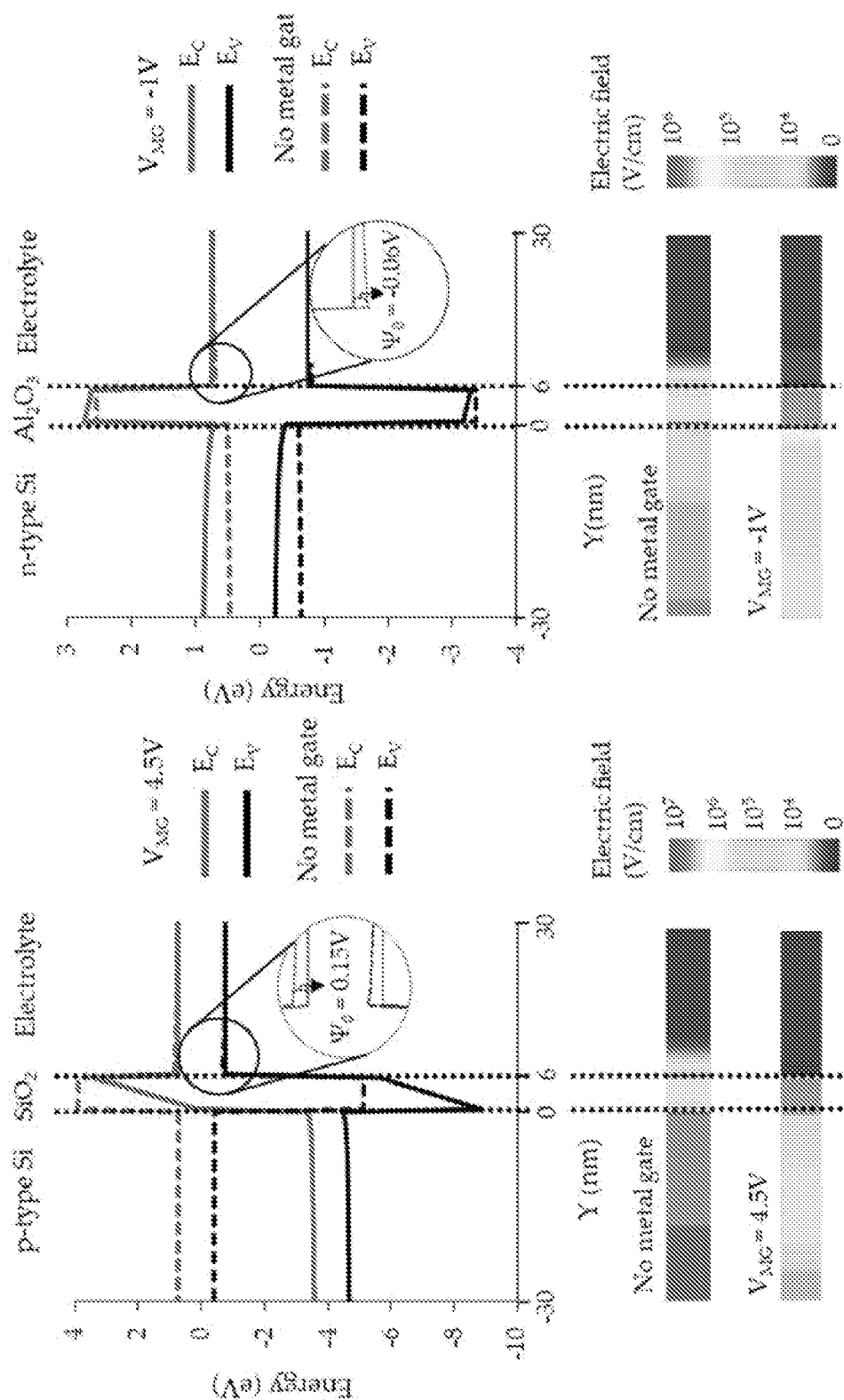
FIG. 6a shows a numerically calculated energy band diagram for a p-type Si—$SiO_2$-electrolyte and a metallic electrode.
FIG. 6b shows an energy band diagram of n-type Si—Al2O3-electrolyte for a non-metal gate with metal gate biasing $V_{mg}=-1V$.
Figures 6C, 6D:
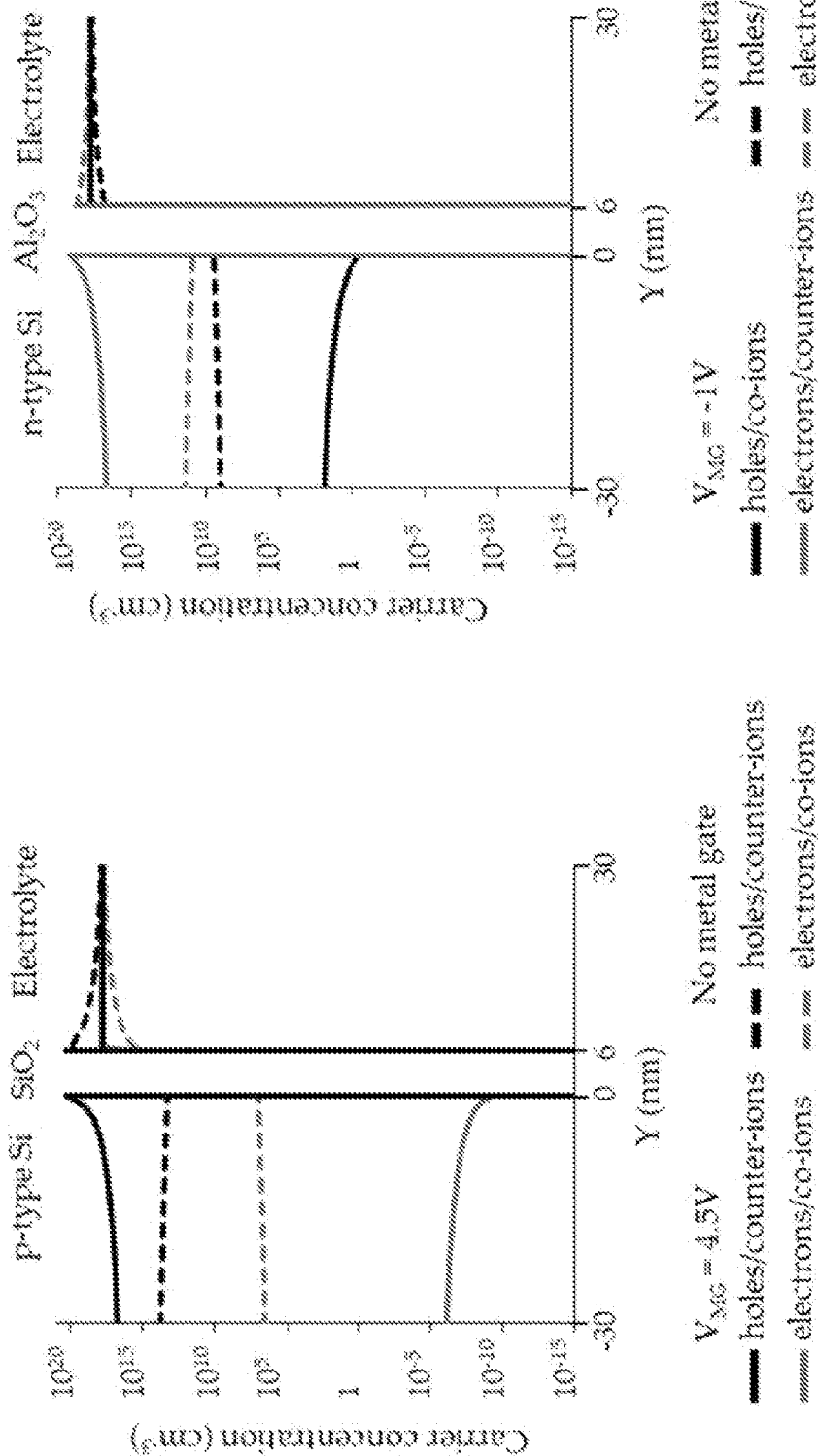
FIG. 6c shows numerical calculations of the corresponding distribution of electrons/anions and holes/cations in p-type Si—SiO2-electrolyte for a non-metal gate with metal gate biasing $V_{mg}=4.5V$.
FIG. 6d shows numerical calculation results of the corresponding distribution of electrons/anions and holes/cations in an n-type Si—Al2O3-electrolyte for a non-metal gate and metal gate biasing $V_{mg}=-1V$.

The inventors also examined the effect of $\sigma_0$ polarity on $V_{mg}$, and for this purpose, two different gateox materials were considered: (a) $SiO_2$ gateox with $\sigma_0=-1.4\times10^{13}$ q cm$^{-2}$; and (b) $Al_2O_3$ gateox with $\sigma_0=+3.2\times10^{12}$ q cm$^{-2}$ both for pH7 and $c_0=1$ mM. FIG. 6a shows a numerically calculated energy band diagram for a p-type Si—$SiO_2$-electrolyte and a metallic electrode, for $V_{mg}=4.5V$. The inset shows a magnified image of the energy band diagram at the EOI, and the electric field distribution with and without $V_{mg}$ is presented below the band diagrams. In this case, for $SiO_2$ and negative $\sigma_0$, the metal gate biasing of $V_{mb}=4.5V$ removes the excess counter-ions at the EOI such that the negative $\sigma_0$ is fully compensated by the accumulation of holes at the front interface. Therefore, for the case of negative $\sigma_0$, the preferred SOI doping is p-type as the hole majority carriers provide ample of positive charge to counterbalance the negative $\sigma_0$. This is evident in FIG. 6a in which for no metal gate biasing, an approximate flat-band condition prevails at the front interface and an upward band bending is evident at the EOI which reflects the accumulation of counter-ions. This is also reflected in the electric field distribution where the front interface electric field is relatively small and a larger electric field is present at the EOI. For $V_{mg}=4.5V$, the front interface flat-band condition is replaced by an upward band bending which reflects hole accumulation at the front interface. On the other hand, at the EOI, $V_{mg}=4.5V$ forces a flat-band condition (shift of 150 mV) which reflects a decrease of 150 mV in $\Psi_0$, as shown in the inset, and yields the desired condition $\lambda_{sc}=\lambda_D$. This is also reflected in the redistribution of the electric fields where the field increases at the front interface and decreases to zero at the EOI as for the bulk quasi-neutral region. FIG. 6c shows the respective mobile charge distributions on both sides of the gateox.

In brief: FIGS. 6a to 6d show numerically calculated results. FIG. 6a shows an energy band diagram of p-type Si—$SiO_2$-electrolyte for no metal gate and metal gate biasing $V_{mg}=4.5V$. Inset: band bending at the $SiO_2$-electrolyte interface. The surface potential $\Psi_0=0.15V$ which corresponds to 1 mM ionic concentration at pH7. FIG. 6b shows an energy band diagram of n-type Si-Al2O3-electrolyte for a non-metal gate with metal gate biasing $V_{mg}=-1V$. Inset: band bending at the Al2O3-electrolyte interface. The surface potential $\Psi_0=-0.06V$ which corresponds to 1 mM ionic concentration at pH7. FIG. 6c shows numerical calculations of the corresponding distribution of electrons/anions and holes/cations in p-type Si-SiO2-electrolyte for a non-metal gate with metal gate biasing $V_{mg}=4.5V$; and, FIG. 6d shows numerical calculation results of the corresponding distribution of electrons/anions and holes/cations in an n-type Si—Al2O3-electrolyte for a non-metal gate and metal gate biasing $V_{mg}=-1V$.

FIG. 6b shows a numerically calculated energy band diagram for an n-type Si—$Al_2O_3$-electrolyte for a metallic electrode and $V_{mg}=-1V$. The inset shows a magnified image of the energy band diagram at the EOI, and the electric field distribution with and without $V_{mg}$ is presented below the band diagrams. In this case, for $Al_2O_3$ and positive $\sigma_0$, the metal gate biasing of $V_{mg}=-1V$ removes the excess counter-ions at the EOI such that the positive $\sigma_0$ is fully compensated by the accumulation of electrons at the front interface. Therefore, for positive $\sigma_0$, the preferred SOI doping is n-type as the electron majority carriers provide ample of negative charge to counterbalance the positive $\sigma_0$. This is evident in FIG. 6b in which for non-metal gate biasing, an approximate flat band condition prevails at the front interface and a downward band bending is evident at the EOI which reflects the accumulation of counter-ions. This is also reflected in the electric field distribution where the front interface electric field is relatively small and a larger electric field is present at the EOI. For $V_{mg}=-1V$, the front interface flat-band condition is replaced by a downward band bending which reflects electron accumulation at the front interface. On the other hand, at the EOI, $V_{mg}=-1V$ forces a flat-band condition which reflects an increase of 60 mV in $\Psi_0$, as shown in the inset, and yields the desired condition $\lambda_{sc}=\lambda_D$. This is also reflected in the redistribution of the electric fields where the field increases at the front interface and decreases to zero at the EOI as for the bulk quasi-neutral region. FIG. 6d shows the respective mobile charge distributions on both sides of the gateox.

The inventors also demonstrated how the suggested approach for electrostatic management of the EOI can be used for biosensing applications. The invention enjoys the benefit of FD-SOI which implies an electrostatic coupling between the front and back interfaces. The inventors solved the Poisson equation for the SOI under full-depletion approximation with boundary conditions as $d\Psi(x)/dx=0$ and $\Psi(x)=\Psi_b$ both for $x=0$ where $\Psi(x)$ is the SOI 1D potential distribution, $d\Psi(x)/dx$ is the SOI 1D electric field distribution, $x=0$ marks the back interface of the SOI and $\Psi_b$ is the back interface potential. This yields the electrostatic coupling between the front and back interfaces:

$$\Psi_v = q\, N_A t_{si}^2 / 2\varepsilon_{si} + \Psi_b \quad (8)$$

where $\varepsilon_{si}$ is the dielectric constant of silicon. Also, as described above, the SOI doping species is selected given the polarity of $\sigma_0$ to ensure that the front interface is always accumulated either with or without the metal gate biasing. In this case, only the bottom channel is available for conduction as the front channel is closed (=accumulated), and therefore any shift in back interface potential ($\Delta\Psi_b$) is equal to the measurable quantity of the back interface threshold voltage ($V_{Tb}$).

Figure 7A:
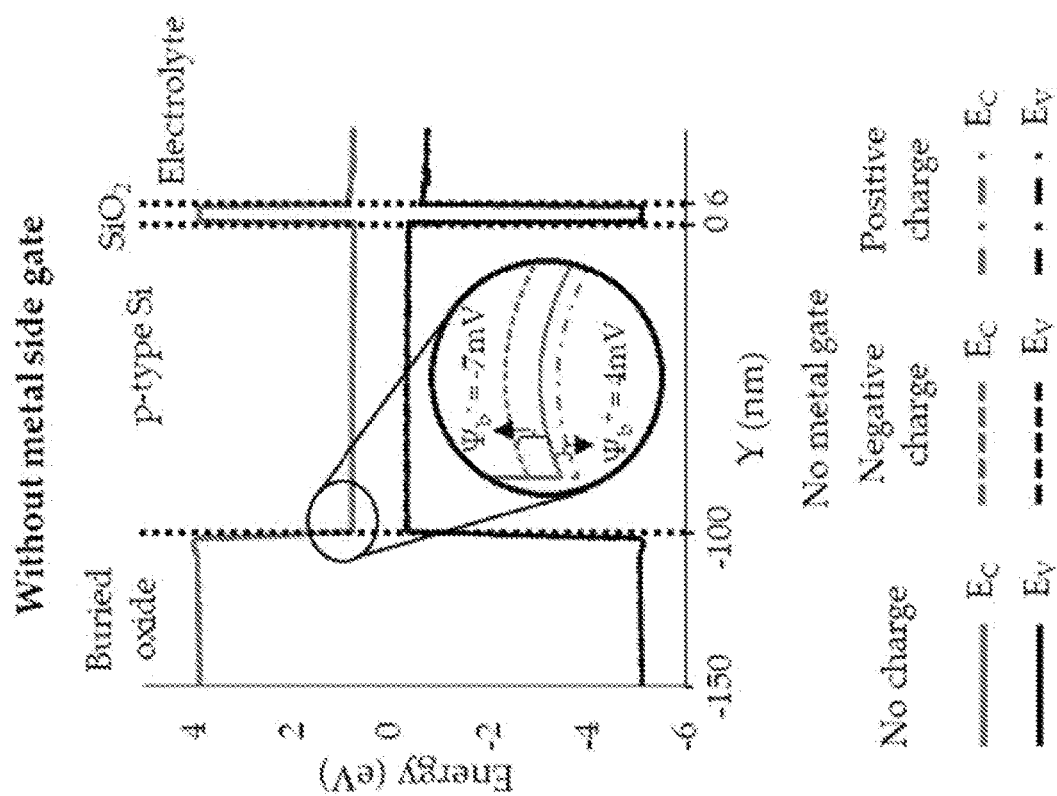
FIG. 7a shows the energy band diagram of the EIS system without the metal electrode (as in FIG. 3a)
Figure 7B:
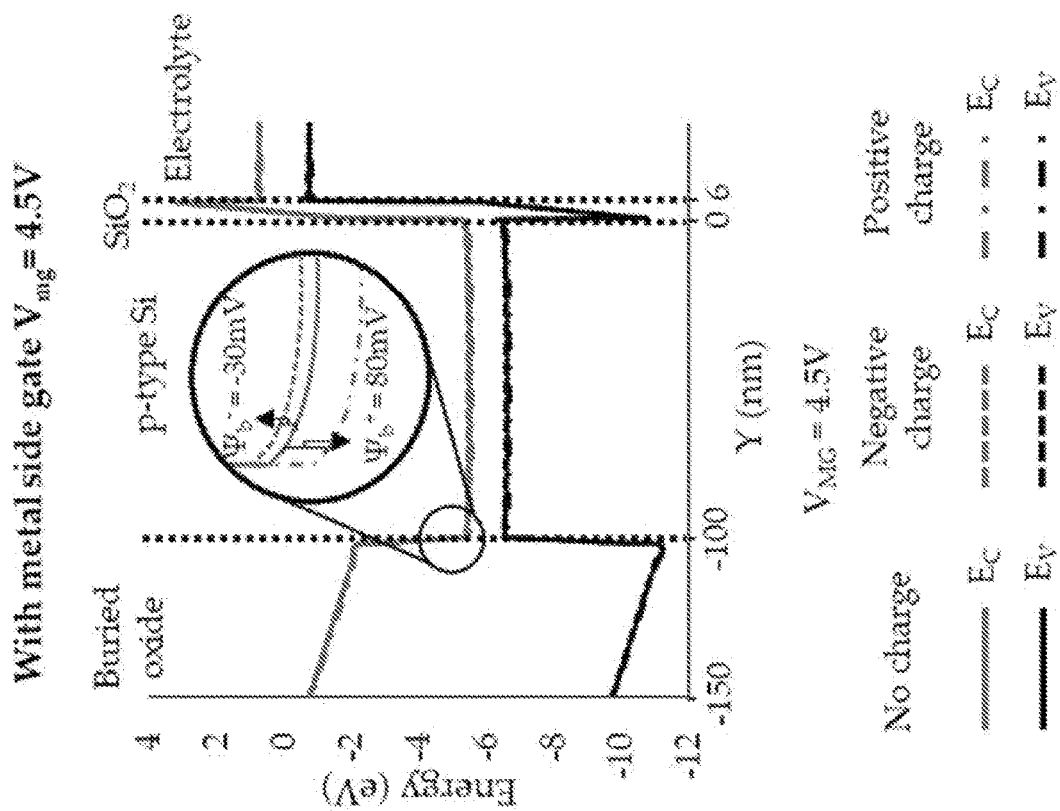
FIG. 7b presents the same situation of FIG. 7a for positive and negative biomolecules on the gateox, but this time with a metal electrode.

The inventors considered two cases: in a first case the inventors emulated a 10 nm thick biomolecular layer having a volume charge density of $+1\times10^{19}$q cm$^{-3}$ on top of the gateox, and in a second case the inventors considered the same volume charge density with a negative polarity. FIG. 7a shows the energy band diagram of the EIS system without the metal electrode (as in FIG. 3a). It was noted that the introduction of negative or positive biomolecules on the gateox has negligible effects on $V_{Tb}$ as $\Delta\Psi_b^-=-7$ mV and $\Delta\Psi_b^+=4$ mV respectively. These shifts in $\Psi_b$ extend throughout the SOI due to the electrostatic coupling between the front and back interfaces for FD-SOI. On the other hand, FIG. 7b presents the same for positive and negative biomolecules on the gateox, but this time the metal electrode (FIG. 4a) was used with $V_{mb}=4.5$V. The enhancement in $V_{Tb}$ shift with $\Delta\Psi_b^-=-30$ mV and $\Delta\Psi_b=80$ mV was noted, respectively. The origin of the enhancement in $V_{Tb}$ shift was ascribed to the removal of excess counter-ions from the EOI, effectively increasing the $\lambda_{sc}$ at the EOI, and 'exposing' more of the target biomolecules to the field-effect functionality of the device.

While some embodiments of the invention have been described by way of illustration, it will be apparent that the invention can be carried into practice with many modifications, variations, and adaptations, and with the use of numerous equivalent or alternative solutions that are within the scope of persons skilled in the art, without departing from the spirit of the invention or exceeding the scope of the claims.

The invention claimed is:

1. An integrated circuit lab-on-chip bio-sensor, comprising:
 a fluid compartment configured to receive a fluid;
 a sensing layer at a bottom of the fluid compartment, the sensing layer having a top surface comprising molecules that are sensitive to target molecules of the fluid;
 a fully depleted Silicon on Insulator (SOI) FET-type structure comprising a gate-oxide (gateox) layer, a fully depleted SOI layer, and a buried-oxide (box) layer;
 a readout structure within said fully depleted SOI structure, said readout structure being in communication with said sensing layer, the readout structure being configured to output a signal which is proportional to sensing concentration of the target molecules by said sensing layer; and
 at least one isolated electrode electrically isolated from the fluid compartment, each of said at least one isolated electrode being configured, when biased, to apply an electric field within said fully depleted SOI layer that affects at least the interface between the sensing layer and the fluid to reduce or eliminate excess ion concentration along said interface during sensing,
 wherein said sensing layer is directly attached at its bottom to said gateox layer, and wherein the gateox layer is directly attached at its bottom to the fully depleted SOI layer of the fully depleted SOI structure, and
 wherein the position of each of said at least one isolated electrode is one of: (a) on top of the sensing layer, or (b) embedded within said fully depleted SOI layer, or (c) on top of the gateox layer.

2. The bio-sensor of claim 1, wherein the at least one isolated electrode is positioned on top of the sensing layer.

3. The bio-sensor of claim 1, wherein said at least one isolated electrode is a metal electrode.

4. The bio-sensor of claim 1, wherein said readout structure comprises said gate-oxide (gateox) layer positioned on top of said fully depleted SOI layer.

5. The bio-sensor of claim 1, wherein said fully depleted SOI structure comprises said fully depleted SOI layer, said box layer, a handle layer, and a back-gate layer.

6. The bio-sensor of claim 1, wherein the at least one isolated electrode is embedded within said fully depleted SOI layer or positioned on top of the gateox layer.

7. The bio-sensor of claim 1, wherein said sensitive molecules within the sensing layer are receptor molecules that are designed to capture the target molecules from said fluid.

8. The bio-sensor of claim 1, further comprising one or more non-isolated electrodes on top of the sensing layer, each of said one or more non-isolated electrodes being configured to have contact with the fluid.

9. The bio-sensor of claim 8, wherein said one or more non-isolated electrodes comprise a plurality of non-isolated electrodes, and wherein each of said plurality of non-isolated electrodes on top of the sensing layer is configured to receive voltage that, when supplied, causes a surface current between two or more of said plurality of non-isolated electrodes, or a fluid current between one or more of said plurality of non-isolated electrodes and one or more reference or counter electrodes that are positioned on a cover of said fluid compartment, thereby to affect interaction of the sensitive molecules within the sensing layer and the target molecules within the fluid.

10. The bio-sensor of claim 1, wherein the readout structure is selected from a FET-type, capacitance-voltage measurement, or electrochemical impedance spectroscopy.

11. The bio-sensor of claim 1, wherein the fluid compartment comprises a fluid inlet and a fluid outlet that are configured to support a fluid flow through the fluid compartment.

12. A method of operating a lab-on-chip bio-sensor, said bio-sensor comprising a fluid compartment, a sensing layer, and a readout structure, the method comprising:
 providing fluid at said fluid compartment;
 providing one or more isolated electrodes that are isolated from the fluid;
 effecting via said one or more isolated electrodes an electric field (E) in a region which includes at least an interface between the sensing layer and the fluid;
 wherein the lab-on-chip bio-sensor is a fully depleted Silicon on Insulator (SOI) FET-type structure comprising a gate-oxide (gateox) layer, a fully depleted SOI layer, and a buried-oxide (box) layer;

wherein said sensing layer is directly attached at its bottom to the gateox layer, and wherein the gateox layer is directly attached at its bottom to the fully depleted SOI layer of the bio-sensor;

wherein said electric field (E) is effected within said fully depleted SOI layer and spans to said interface between the sensing layer and the fluid, and wherein the position of each said one or more isolated electrode is one of: (a) on top of the sensing layer, (b) embedded within said fully depleted SOI layer, or (c) on top of the gateox layer.

13. The method of claim 12, wherein said electric field (E) is configured to eliminate accumulation of ions in the interface between the sensing layer and the fluid.

14. The method of claim 13, wherein said electric field (E) and said elimination of the accumulation of ions at the interface between the sensing layer and the fluid also affects one or more of: (a) the pH level at the interface to match to the pH at the bulk of the fluid; (b) reduction of a surface ion density to match an ion density at the bulk of the fluid; and (c) reduction of an electric field at the interface to match an electric field at the bulk of the fluid.

15. The method of claim 13, wherein said elimination of the accumulation of ions increases a Debye screening length.

16. The method of claim 13, wherein said elimination of the accumulation of ions produces a homogenous region within the entire solution in terms of charge carries.

17. The method of claim 12, further comprising providing receptors at the sensing layer that are configured to selectively capture target molecules within the fluid.

18. The method of claim 17, further comprising generating current flows through the fluid to manipulate orientations of the receptors and/or the target molecules, thereby to increase a probability of the target molecules capturing by the receptors.

19. The method of claim 18, wherein said current flows are generated between two or more non-isolated electrodes, at least some of them being located on the sensing layer or on a cover of said fluid compartment.

20. The method of claim 19, wherein said current flows are selected from: (a) surface currents along the surface of the sensing layer between two or more of non-isolated electrodes on top of the sensing layer; and (b) fluid current flows between one or more of non-isolated electrodes on top of the sensing layer and one or more non-isolated electrodes on the cover of the fluid compartment of the bio-sensor.

21. The method of claim 19, wherein said current flows through the fluid are provided in a first stage to manipulate interactions of the receptors and/or the target molecules, and said electric field is provided in a second, readout stage to increase a Debye length at the interface.

22. The method of claim 18, wherein said currents flows are either DC or AC currents.

23. The method of claim 12, comprising providing in a first stage a voltage to the one or more isolated electrodes to affect surface electric fields, surface pH level, or surface ion density, and in a second readout stage providing said electric field to increase a Debye length at the interface.

24. The method of claim 12, wherein a voltage which is provided to the one or more isolated electrodes is DC or AC voltage.

* * * * *